(12) United States Patent
Kung et al.

(10) Patent No.: US 8,747,809 B2
(45) Date of Patent: Jun. 10, 2014

(54) SINGLE DIASTEREOMERS OF 4-FLUOROGLUTAMINE AND METHODS OF THEIR PREPARATION AND USE

(75) Inventors: Hank F. Kung, Springfield, PA (US); Craig B. Thompson, Merion Station, PA (US); Wenchao Qu, Ardmore, PA (US); Karl Ploessl, Wilmington, DE (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 51 days.

(21) Appl. No.: 13/389,521

(22) PCT Filed: Aug. 13, 2010

(86) PCT No.: PCT/US2010/045470
§ 371 (c)(1),
(2), (4) Date: Apr. 24, 2012

(87) PCT Pub. No.: WO2011/020018
PCT Pub. Date: Feb. 17, 2011

(65) Prior Publication Data
US 2012/0288444 A1    Nov. 15, 2012

Related U.S. Application Data

(60) Provisional application No. 61/233,875, filed on Aug. 14, 2009.

(51) Int. Cl.
*A61K 51/00* (2006.01)
*C07D 209/48* (2006.01)

(52) U.S. Cl.
USPC ....... 424/1.89; 424/9.365; 548/403; 548/530; 548/537

(58) Field of Classification Search
USPC ............... 424/1.89, 9.365; 548/403, 530, 537
See application file for complete search history.

(56) References Cited

U.S. PATENT DOCUMENTS

| | | | |
|---|---|---|---|
| 6,040,422 A | 3/2000 | Carpino et al. | |
| 2004/0210060 A1 | 10/2004 | Delplanche et al. | |

FOREIGN PATENT DOCUMENTS

| | | |
|---|---|---|
| CA | 2667395 | 5/2008 |
| EP | 1 923 382 | 5/2008 |
| EP | 2 123 620 | 11/2009 |
| EP | 2123620 | * 11/2009 |
| WO | WO 2008/052788 | 5/2008 |
| WO | WO 2009/141090 | 11/2009 |

OTHER PUBLICATIONS

Adlington et al., "The synthesis of pyrimidin-4-yl substituted α-amino acids. A versatile approach from alkynyl ketones," J. Chem. Soc., Perkin Trans. 1, 1999, Issue 8, 855-866.

Armstrong et al., "A new method for the preparation of tertiary butyl ethers and esters," Tetrahedron Lett., 1988, 29(20), 2483-2486.

Bergmeir et al., "Chirospecific synthesis of (1S,3R)-1-amino-3-(hydroxymethyl)cyclopentane, precursor for carbocyclic nucleoside synthesis. Dieckmann cyclization with an .alpha.-amino acid," The Journal of Organic Chemistry, Apr. 1993, 58(9), 2369-2376.

Costa et al., "An improved approach for the synthesis of α,α-dialkyl glycine derivatives by the Ugi-Passerini reaction," Org. Biomol. Chem., Mar. 2003,1(9), 1475-1479.

Couturier et al., "Fluorinated tracers for imaging cancer with positron emission tomography," European Journal of Nuclear Medicine and Molecular Imaging, Aug. 2004, 31(8), 1182-1206.

Dave et al., "gamma-Fluorinated analogs of glutamic acid and glutamine," Amino Acids, Jan. 2003, 24(3), 245-261.

Dess et al., "Readily accessible 12-I-5 oxidant for the conversion of primary and secondary alcohols to aldehydes and ketones," The Journal of Organic Chemistry, Nov. 1983, 48(22), 4155-4156.

Dhaon et al., "Esterification of N-protected .alpha.-amino acids with alcohol/carbodiimide/4-(dimethylamino)pyridine. Racemization of aspartic and glutamic acid derivatives," The Journal of Organic Chemistry, May 1982, 47(10), 1962-1965.

Domling, A., "Recent Developments in Isocyanide Based Multicomponent Reactions in Applied Chemistry," Chem. Rev., Jan. 2006, 106(1), 17-89.

International Patent Application No. PCT/US2010/045470: International Search Report and Written Opinion dated Oct. 15, 2010, 8 pages.

Marshall et al., "Preparation of 4-Oxo-l-norvaline via Diazomethane Homologation of β-Aspartyl Semialdehyde," The Journal of Organic Chemistry, Nov. 1997, 62(23), 8243-8246.

Masaki et al., "A new method for the removal of chloroacetyl groups," Journal of the American Chemical Society, Jul. 1968, 90(16), 4508-4509.

Mercer, J. R., "Molecular imaging agents for clinical positron emission tomography in oncology other than fluorodeoxyglucose (FDG): applications, limitations and potential," Journal of Pharmacy & Pharmaceutical Sciences, Jun. 2007, 10(2), 180-202.

Miller et al., "Synthesis of 11C, 18F, 15O, and 13N radiolabels for positron emission tomography," Angewandte Chemie International Edition, 2008, 47(47), 8998-9033.

Naruto et al., "Synthesis of Prostaglandins and their congeners I. (+)-11-deoxy-11α-hydroxymethyl prostaglandin F2α from aucubin," Tetrahedron Lett., 1979, 20(3), 251-254.

Pigge et al., "Ruthenium-Coordinated Spirolactams via Intramolecular Nucleophilic Addition to η6-Arene Metal Complexes," Organometallics, Sep. 2002, 21(21), 4505-4512.

(Continued)

*Primary Examiner* — Michael G Hartley
*Assistant Examiner* — Jagadishwar Samala
(74) *Attorney, Agent, or Firm* — Baker & Hostetler LLP

(57) ABSTRACT

The present invention is directed single diasteromers of 4-fluoroglutamine having a diastereomeric excess of at least 80%. Methods of preparing the single diastereomers are also described, as well as methods of using the single diastereomers of radiolabeled 4-fluoroglutamine as imaging agent is also described.

25 Claims, 13 Drawing Sheets

(56) References Cited

OTHER PUBLICATIONS

Qu et al., "Facile Synthesis of Optically Pure 4-Fluoro-L-glutamines: Skeleton Assembly via Passerini Reaction and Fluorination by TASF," Departments of Radiology and Pharmacology, University of Pennsylvania, Aug. 2009, 1-13.

Ramsamy et al., "Synthesis of N-t-Boc-L-a-aminoadipic Acid 1-t-Butyl 6-Ethyl Ester from L-Aspartic Acid: A New Route to L-a-Aminoadipic Acid," Synthesis, 1982, Issue 1, 42-43.

Tolman et al., "Chemistry of 4-fluoroglutamic acid. Part 3. Preparation of the diastereomers of 4-fluoroglutamine and 4-fluoroisoglutamine. An enzymatic access to the antipodes of 4-amino-2-fluorobutyric acid," Journal of Fluorine Chemistry, Jan. 2000, 101(1), 5-10.

Wernic et al., "Enantiospecific synthesis of L-.alpha.-aminosuberic acid. Synthetic applications in preparation of atrial natriuretic factor analogs," The Journal of Organic Chemistry, Aug. 1989, 54(17), 4224-4228.

Wise et al., "Myc regulates a transcriptional program that stimulates mitochondrial glutaminolysis and leads to glutamine addiction," PNAS, Dec. 2008, 105(48), 18782-18787.

Yang et al., ".beta.-Phenacyl ester as a temporary protecting group to minimize cyclic imide formation during subsequent treatment of aspartyl peptides with hydrofluoric acid," The Journal of Organic Chemistry, Mar. 1976, 41(6), 1032-1041.

* cited by examiner

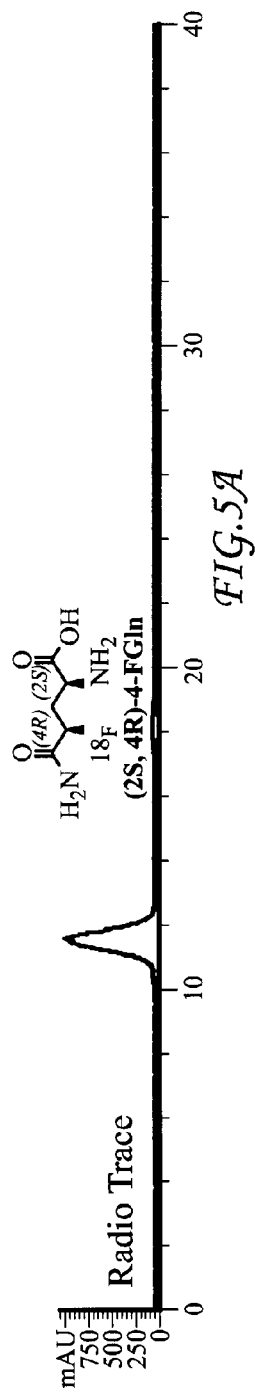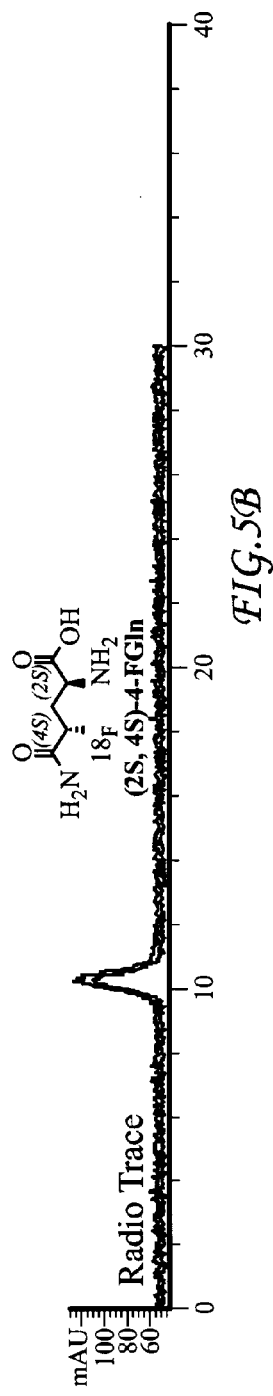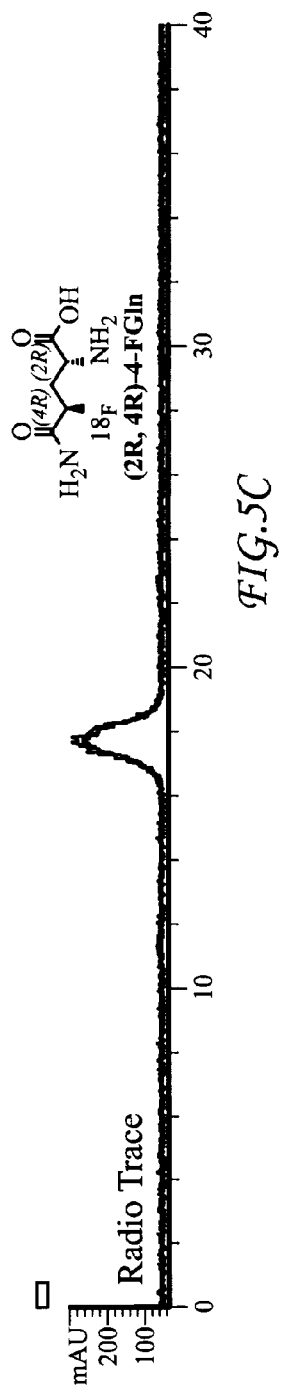

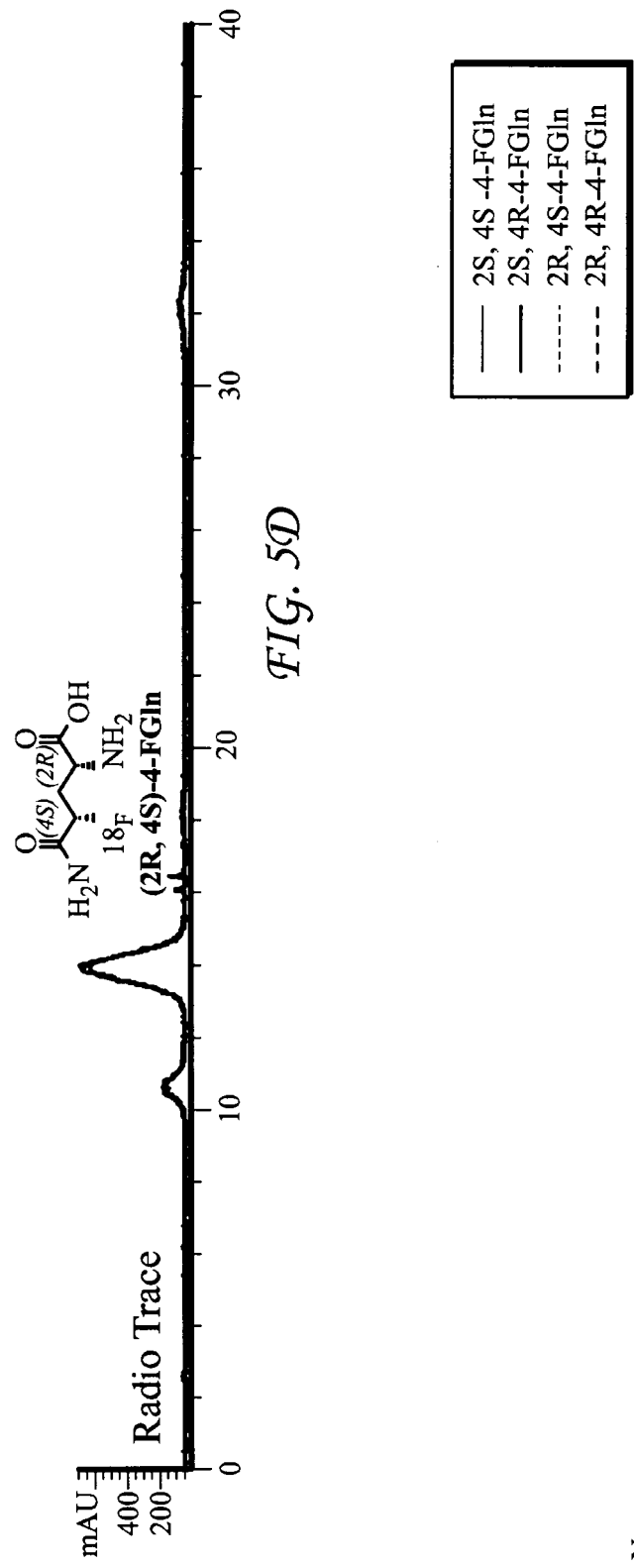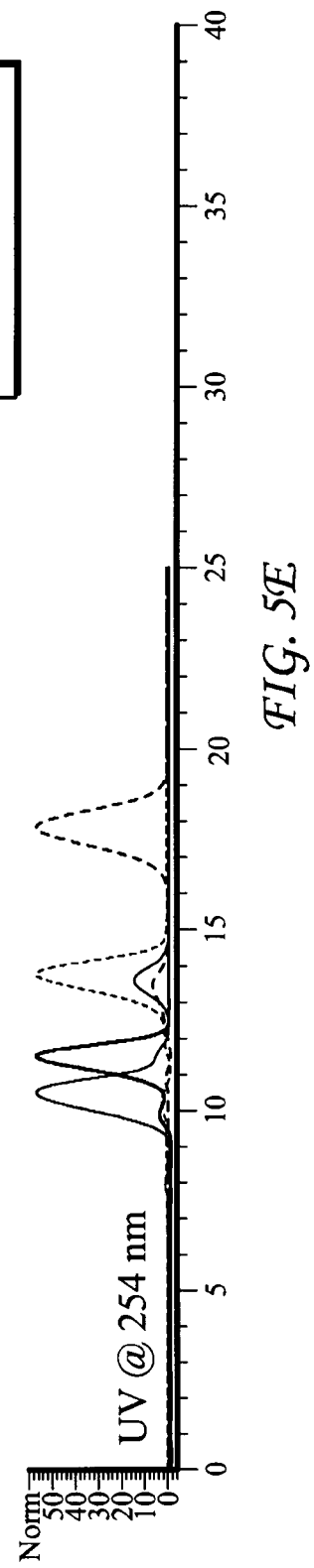
FIG. 5D
FIG. 5E

HPLC: OD, Hexanes/ethanol 98.5/1.5, 1.2 mL/min

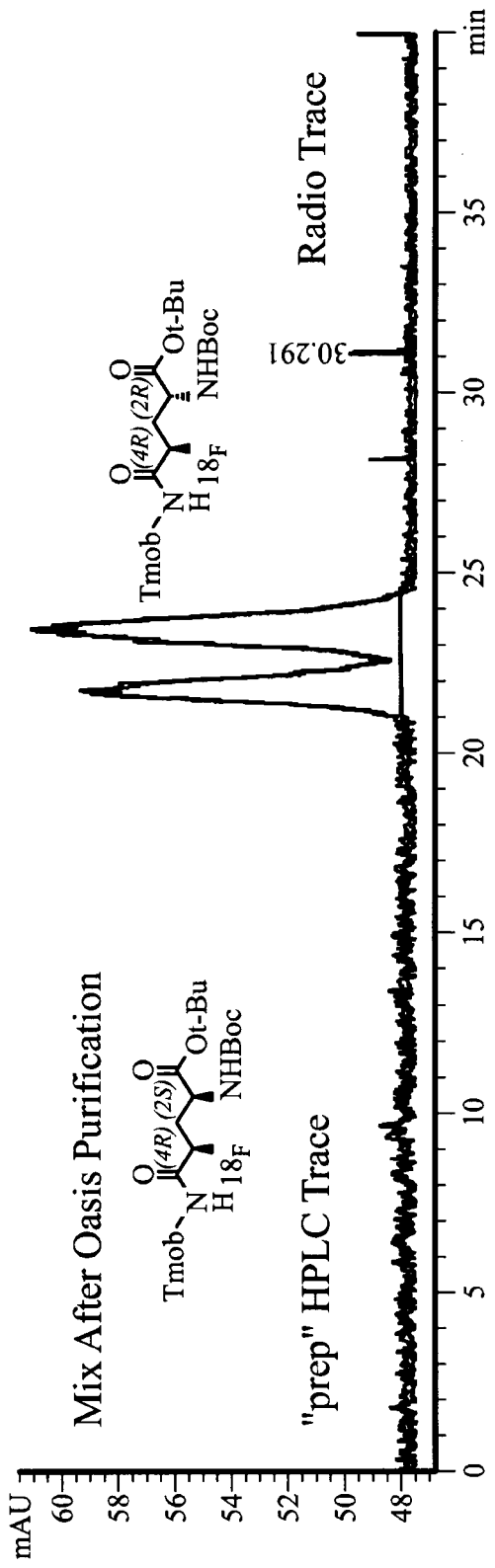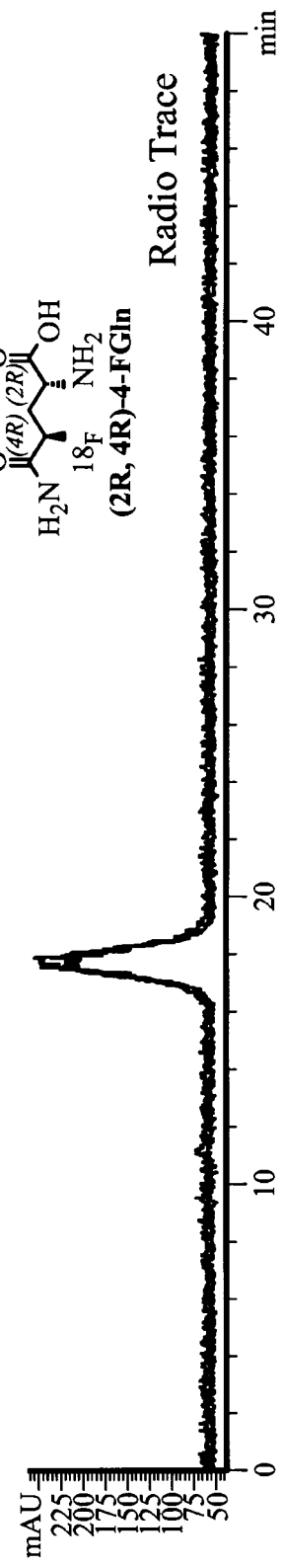
FIG. 14
FIG. 15A

SINGLE DIASTEREOMERS OF 4-FLUOROGLUTAMINE AND METHODS OF THEIR PREPARATION AND USE

CROSS-REFERENCE TO RELATED APPLICATIONS

This application is the National Stage of International Application No. PCT/US2010/045470, filed Aug. 13, 2010, which claims the benefit of U.S. Provisional Application No. 61/233,875 filed Aug. 14, 2009, the disclosures of which are incorporated herein by reference in their entireties.

TECHNICAL FIELD

This application is directed to improved methods for the preparation of 4-fluoro-glutamines.

BACKGROUND

Fluorine-substituted amino acids have application in peptide-based drug design and protein engineering and also demonstrate application in PET imaging for diagnosis of cancer. Since 2-[$^{18}$F]fluoro-2-deoxy-D-glucose (FDG) was successfully developed as a positron emission tomography (PET) tracer and used for routine cancer imaging, designing and developing fluorine-18 radiolabeled agents for diagnosis of various diseases has emerged as a very active research area. See, e.g., Mercer, J. R., Molecular imaging agents for clinical positron emission tomography in oncology other than fluorodeoxyglucose (FDG): applications, limitations and potential. *Journal of Pharmacy & Pharmaceutical Sciences* 2007, 10, (2), 180-202; Couturier, O.; Luxen, A.; Chatal, J.-F.; Vuillez, J.-P.; Rigo, P.; Hustinx, R., Fluorinated tracers for imaging cancer with positron emission tomography. *European Journal of Nuclear Medicine and Molecular Imaging* 2004, 31, (8), 1182-1206.; and Miller, P. W.; Long, N.J.; Vilar, R.; Gee, A. D., Synthesis of $^{11}$C, $^{18}$F, $^{15}$O, and $^{13}$N radiolabels for positron emission tomography. *Angewandte Chemie, International Edition* 2008, 47, (47), 8998-9033.

The mechanism of cancer imaging by FDG is based upon the avidity of tumor cells toward energy source—glucose, i.e., the increased glycolysis in tumor cells. Recent reports suggest that glutamine ($NH_2C(O)CH_2CH_2CHNH_2C(O)OH$, Gln) may also be a source of metabolic energy for cells under stress—glutaminolysis. Wise, D. R.; Deberardinis, R. J.; Mancuso, A.; Sayed, N.; Zhang, X. Y.; Pfeiffer, H. K.; Nissim, I.; Daikhin, E.; Yudkoff, M.; McMahon, S. B.; Thompson, C. B., Myc regulates a transcriptional program that stimulates mitochondrial glutaminolysis and leads to glutamine addiction. *Proc Natl Acad Sci USA* 2008. Accordingly, a need exists to develop Gln and its analogs as metabolic tracers for studying increased tumor metabolism.

There is interest in synthesizing the four diastereomers of $^{18}$F-radiolabeled 4-fluoro-L-glutamines (4-FGln) ([$^{18}$F]1, 2, 3, and 4) and further assessing their biological properties in various types of tumor cells.

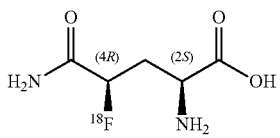

[$^{18}$F]1

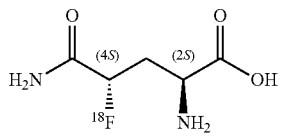

[$^{18}$F]2

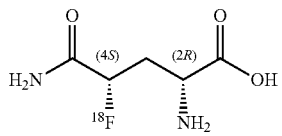

[$^{18}$F]3

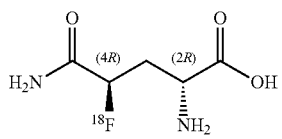

[$^{18}$F]4

In order to validate the preparation of [$^{18}$F]1-4, however, a practical synthesis of the nonradioactive molecules, the so-called "cold standard," first needs to be achieved. Attempts to synthesize various stereospecific fluorinated α-amino acids (F-α-AA) have been reported recently. Dave, R.; Badet, B.; Meffre, P., gamma-Fluorinated analogs of glutamic acid and glutamine. *Amino Acids* 2003, 24, (3), 245-261. Tolman, V.; Sedmera, P., Chemistry of 4-fluoroglutamic acid. Part 3. Preparation of the diastereomers of 4-fluoroglutamine and 4-fluoroisoglutamine. An enzymatic access to the antipodes of 4-amino-2-fluorobutyric acid. *Journal of Fluorine Chemistry* 2000, 101, (1), 5-10. Those syntheses are summarized below in Schemes 1 and 2:

Scheme 1

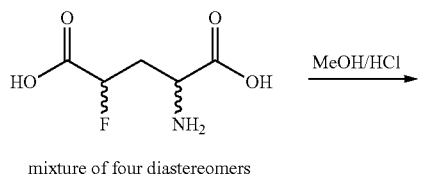

mixture of four diastereomers

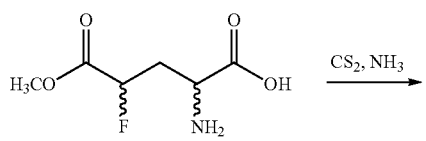

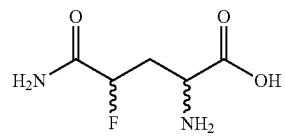

mixture of four diastereomers

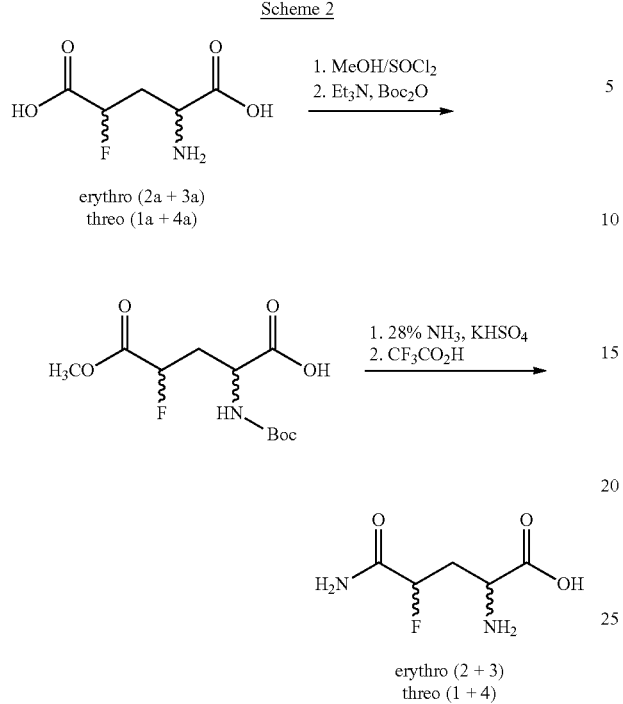

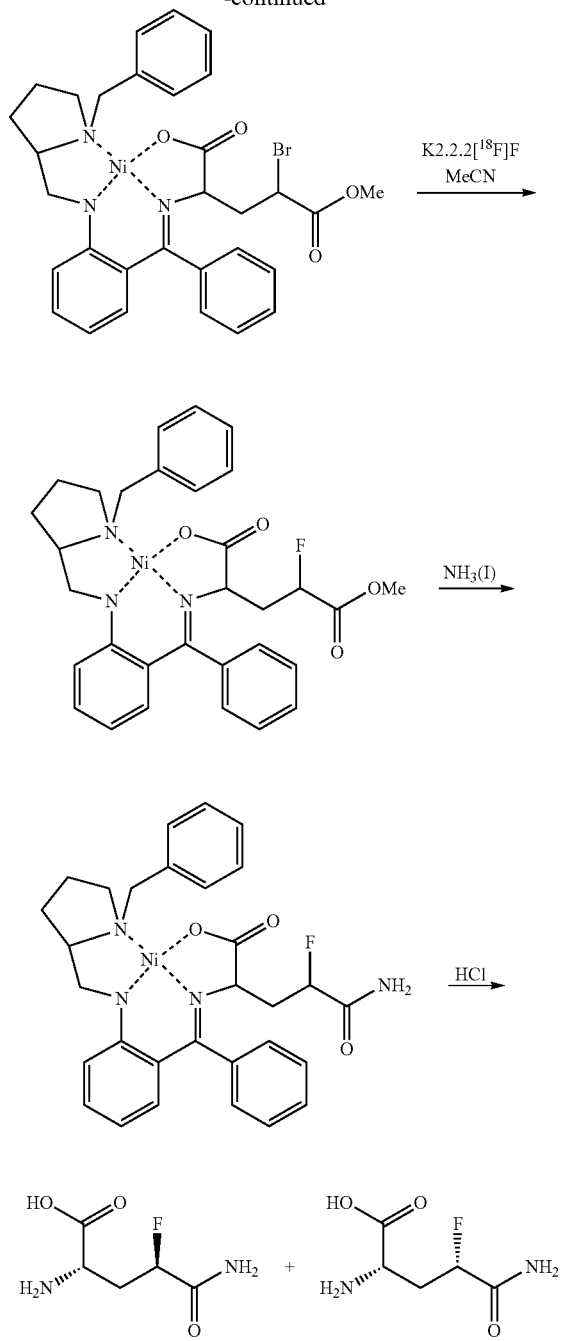

The sequence set forth in Scheme 1 only provides 4-fluoroglutamine as a mixture of four diastereomers, starting from a mixture of 4-fluoroglutamic acids. Diastereomers of 4-fluoroglutamic acid can require up to 11 steps to prepare. The sequence set forth in Scheme 2 starts with a racemic mixture of either erythro or threo 4-fluoroglutamic acids. The racemates are then converted to racemic erythro or racemic threo 4-FGln. Single isomers cannot be prepared according to the method of Scheme 2. Interestingly, Dave, et al. state that "It is worth noting that the same transformation [of Scheme 2] have not yet been applied to the synthesis of enantiomerically pure 4-fluoroglutamine despite the available procedures for the preparation of all four stereomers of 4-fluorogluamic acid.

WO2008/052788 describes the preparation of diastereomeric mixtures of 4-fluoro-L-glutamine, prepared by a metal-catalyzed synthesis using a nickel complex of a glycine-containing Schiff's base and (S)-2-[N—(N-benzylpropyl) amino]benzophenone (BPB) and 3-bromobut-3-enoic acid methyl ester:

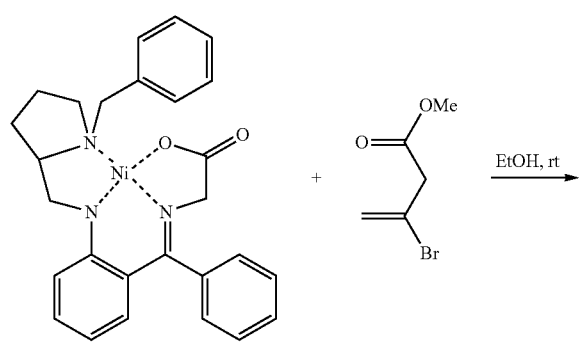

WO2008/-62799, Examples 1 and 2.

Nevertheless, the synthesis of single isomers of each of the four diastereomers of 4-fluoroglutamine has yet to be reported. Moreover, considering that the ultimate goal is to synthesize a radioactive compound, a synthesis that introduces the fluorine atom at a late stage, in contrast to the sequences set forth in Schemes 1 and 2, is advantageous due to the short half life of $^{18}F$ atom ($t_{1/2}$=109.7 min).

SUMMARY

The present invention is directed to single diastereomers of 4-fluoroglutamine

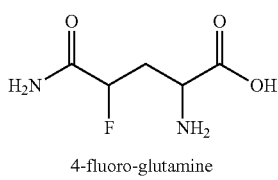

4-fluoro-glutamine a diasteromeric excess of at least 80%, as well as precursors to single isomers of 4-fluoroglutamine.

The present invention is also directed to methods of preparing single diastereomers of 4-fluoroglutamine comprising reacting a single diastereomer of a compound of formula I having a diasteromeric excess of at least 80%

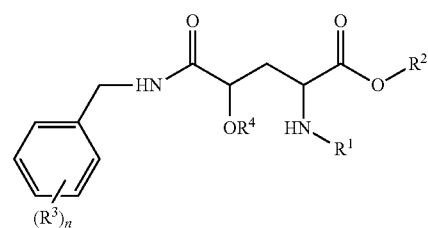

I wherein
$R^1$ is an acid-labile nitrogen protecting group;
$R^2$ is $C_{1-6}$alkyl or $C_{1-6}$cycloalkyl;
each $R^3$ is independently —$OC_{1-6}$alkyl or $C_{1-6}$cycloalkyl;
$OR^4$ is a leaving group; and
n is 0, 1, 2, 3, or 4;
with a fluorinating agent, for a time and under conditions effective to form a single diastereomer of a compound of formula II having a diasteromeric excess of at least 80%

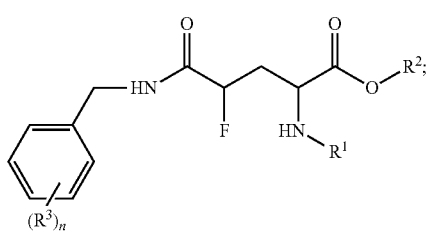

II and
reacting the single diastereomer of the compound of formula II with an acid for a time and under conditions effective to produce the single diastereomer of 4-fluoroglutamine.

Methods of using single isomers of radiolabed 4-fluoroglutamine in imaging cancer are also described.

BRIEF DESCRIPTION OF THE DRAWINGS

FIGS. 5A, 5B, 5C, and 5D depict HPLC profiles of four radio-labeled 4F-Gln embodiments of the invention. The "cold" standards can be ascertained using Chiral Chirex3126 (D-penicillamine) (150×4.6 mm) 1 mM $CuSO_4$, 1 mL/min, 10° C. Using these conditions, compound 2 elutes first, followed by compound 1, 3, and 4. A composite HPLC profile is depicted in FIG. 5E.

FIG. 14 depicts a radioactive HPLC trace of ethanolic solution (mix of [18F]12' and [18F]12a") on Chiral OD column, hexanes/EtOH 98.5/1.5, flowrate 1.2 mL/min.

FIGS. 15A, 15B, and 15C depict HPLC traces of purified [18F]2 ((2S,4S)-4-FGln on chiral column (Chirex 3126 (d)-penicillamine, 1 mM CuSO4 solution, 1 mL/min, Identity was established by coinjection with the cold standard.

DETAILED DESCRIPTION OF ILLUSTRATIVE EMBODIMENTS

Figure 1:
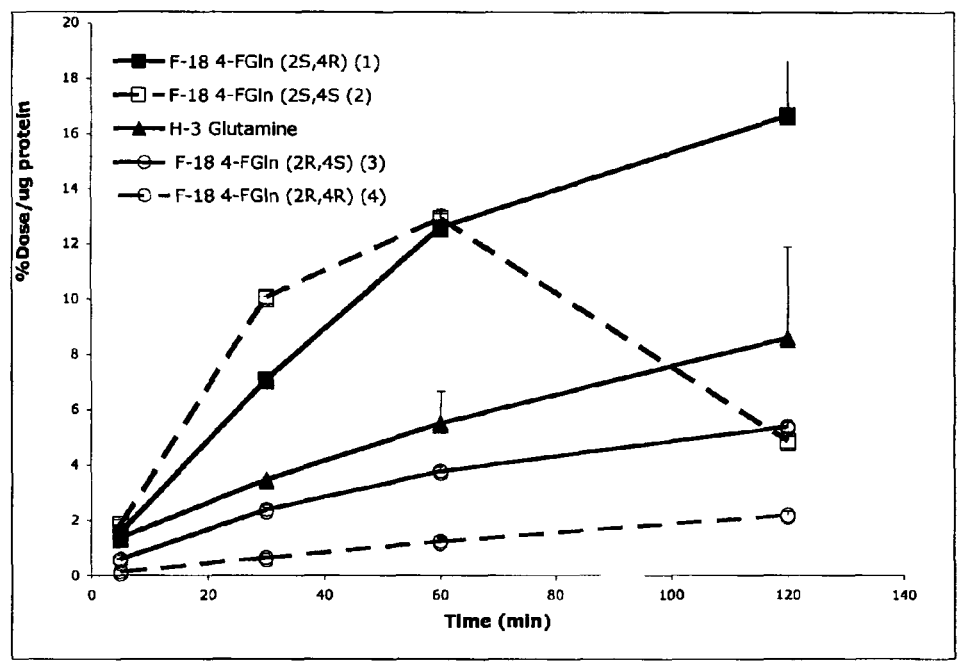
FIG. 1 represents the uptake of compounds 1, 2, 3, and 4 in 9 L cells.

The present invention is directed to single diastereomers of 4-fluoroglutamine diastereomers having a diasteromeric excess of at least 80%. It has been discovered that each single diastereomer has a different reuptake profile as compared to previously prepared mixtures of diastereomers. The single diastereomers of 4-fluoroglutamine are represented below as compounds 1-4. The invention is also directed to single diastereomers of [18F]-labeled 4-fluoroglutamine having a diasteromeric excess of at least 80%. It will be understood by those skilled in the art that reference to 4-fluoro-glutamine includes both non-labeled fluoro-glutamine, and labeled, i.e., [18F]-labeled fluoroglutamine.

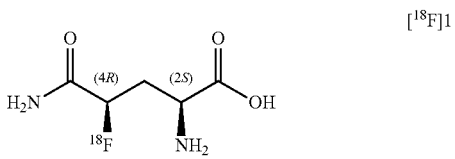

[18F]1

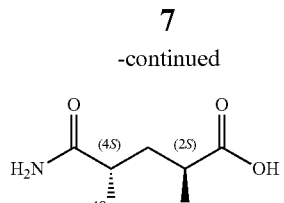

[¹⁸F]2

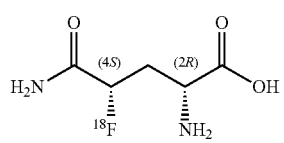

[¹⁸F]3

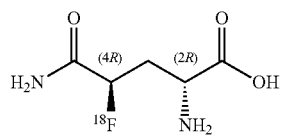

[¹⁸F]4

It is preferred that the single diastereomers of 4-fluoroglutamine have 100% diastereomeric excess. Within the scope of the invention, however, one, two, or three of the other diastereomers of 4-fluoroglutamine may be present with the single diastereomer of 4-fluoroglutamine. In other embodiments, the single diastereomers have a diastereomeric excess of at least 80%. In other embodiments, the single diastereomers have a diastereomeric excess of at least 90%. In other embodiments, the single diastereomers have a diastereomeric excess of at least 98%.

As used herein "diastereomeric excess" refers to the difference between the mole fraction of the desired single diastereomer as compared to the remaining diastereomers in a composition. Diastereomeric excess is calculated as follows:

(amount of single diastereomer)−(amount of other diastereomers)/1

For example, a composition that contains 90% of 1 and 10% of 2, 3, 4, or a mixture thereof has a diastereomeric excess of 80% [(90-10)/1]. A composition that contains 95% of 1 and 5% of 2, 3, 4, or a mixture thereof has a diastereomeric excess of 90% [(95-5)/1]. A composition that contains 99% of 1 and 1% of 2, 3, 4, or a mixture thereof has a diastereomeric excess of 98% [(99-1)/1]. The diastereomeric excess can similarly be calculated for any one of 1, 2, 3, or 4.

Methods of quantifying the amount of each diastereomer of 4-fluoroglutamine, as well as are known in the art. Most preferred methods include high performance liquid chromatography (HPLC), preferably using a chiral column, wherein the area under the curve of each of the peaks for each diastereomer correlates to the amount of each diastereomer present in the sample.

Of particular interest are methods for preparing single diastereomers of 4-fluoro-L-glutamines 1 and 2, as well as the corresponding ¹⁸F-labeled compounds [¹⁸F]1 and [¹⁸F]2:

The methods of the invention include reacting a single diastereomer of a compound of formula I having a diastereomeric excess of at least 80%:

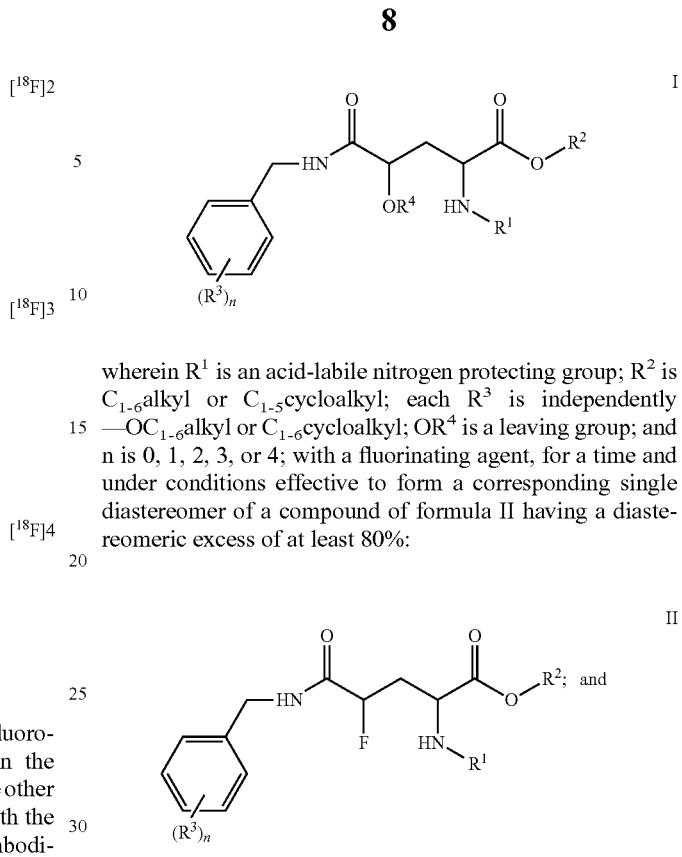

wherein $R^1$ is an acid-labile nitrogen protecting group; $R^2$ is $C_{1-6}$alkyl or $C_{1-5}$cycloalkyl; each $R^3$ is independently —$OC_{1-6}$alkyl or $C_{1-6}$cycloalkyl; $OR^4$ is a leaving group; and n is 0, 1, 2, 3, or 4; with a fluorinating agent, for a time and under conditions effective to form a corresponding single diastereomer of a compound of formula II having a diastereomeric excess of at least 80%:

reacting the single diastereomer of the compound of formula II with an acid for a time and under conditions effective to produce the single diastereomer of 4-fluoroglutamines having a diastereomeric excess of at least 80%. One exemplary acid is trifluoroacetic acid.

Preferably, the compound of formula I is provided as a single diastereomer with none of the other three diastereomers present. In preferred embodiments, the single diastereomer of the compound of formula I has a diastereomeric excess of at least 80%. Preferably, the single diastereomer of the compound of formula I has a diastereomeric excess of at least 90%. Most preferably, the single diastereomer of the compound of formula I has a diastereomeric excess of at least 98%.

In some embodiments, the single diastereomer of the compound of formula I is essentially

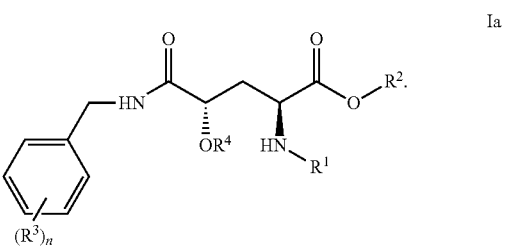

Within the scope of the invention, "essentially" refers to the presence of only one diastereomer having a diastereomeric excess of at least 90%, more preferably 98%.

In other embodiments, the single diastereomer of the compound of formula I is essentially

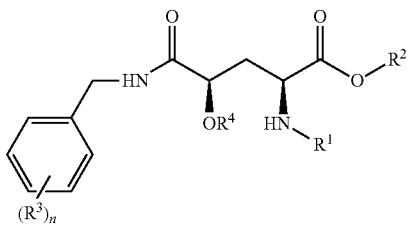

Ib

In yet other embodiments, the single diastereomer of the compound of formula I is essentially

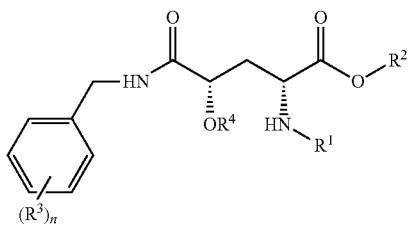

Ic

In still other embodiments, the single diastereomer of the compound of formula I is essentially

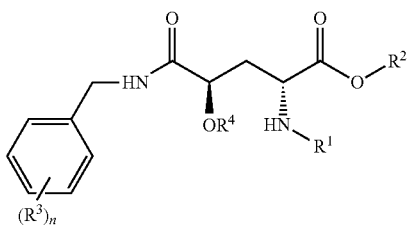

Id

The single diastereomers of compounds of formula I, in particular, compounds Ia, Ib, Ic, and Id, having a diastereomeric excess of at least 80%, preferably 90%, most preferably 98%, are also within the scope of the invention.

Preferably, —OR$^4$ is —Otosylate (—OSO$_2$C$_6$H$_4$-pCH3).

Preferably, the compound of formula II is provided as a single diastereomer with none of the other three diastereomers present. If diastereomeric purity is not preserved in the formation of the compound of formula II, the diastereomers can be separated according to methods known in the art, including HPLC, to afford a single diastereomer of the compound of formula II having a diastereomeric excess of at least 80%. In preferred embodiments, the single diastereomer of the compound of formula II has a diastereomeric excess of at least 80%. Preferably, the single diastereomer of the compound of formula II has a diastereomeric excess of at least 90%. Most preferably, the single diastereomer of the compound of formula II has a diastereomeric excess of at least 98%.

In some embodiments, the single diastereomer of the compound of formula II is essentially

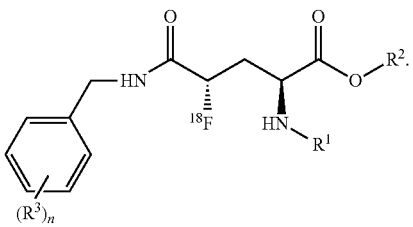

IIa

In other embodiments, the single diastereomer of the compound of formula II is essentially

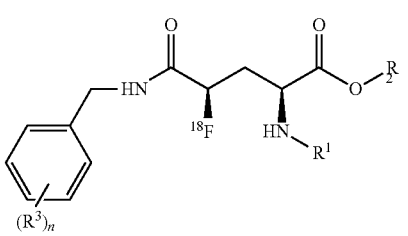

IIb

In yet other embodiments, the single diastereomer of the compound of formula II is essentially

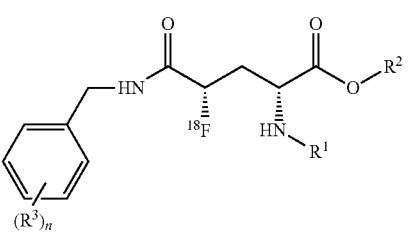

IIc

In still other embodiments, the single diastereomer of the compound of formula II is essentially

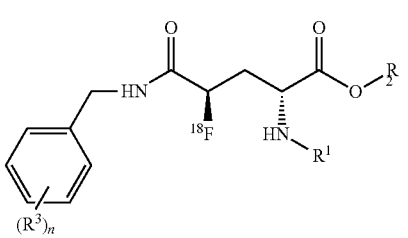

IId

Fluorinating agents are known in the art, per se and suitable fluorinating reagents can be identified by one skilled in the art. Examples of particularly preferred fluorinating agents include hypervalent silicate fluorinating agents, for example, tetrabutylammonium difluorotriphenylsilicate (TBAT), [Bu$_4$N][Ph$_3$SnF$_2$], perfluoro-1-butanesulfonyl fluoride (PBSF), tri(dimethylamino)sulfonium difluorotrimethylsilicate (TASF).

During fluorination, epimerization at the C(2) position is possible, resulting in a loss of diastereomeric excess. In such situations, the diastereomers can be readily separated using conventional methods, for example, HPLC. It has been discovered that moderating the basicity of the fluorination reagent may reduce or eliminate the amount of epimerization. Examples of reagents that can be used to moderate the basicity of the fluorinating agent include 2-mesitylenesulfonic acid and Et₃N—(HF)₃. Preferably, the fluorinating agent is titrated to adjust the pH to about 7-8. Particularly preferred reagents for fluorination are TASF, pH adjusted with Et₃N(HF)₃.

Preferred solvents for the fluorination reaction include tetrahydrofuran, dichloromethane, acetonitrile, and mixtures thereof.

Use of a $^{18}$F-labeled fluorinating reagent will result in the formation of the corresponding $^{18}$F-labeled compound of formula IIa, IIb, IIc, and IId.

Use of certain fluorinating reaction conditions may, while successfully resulting in the incorporation of fluorine, result in a loss of diastereomeric excess. In such situations, the diastereomers can be readily separated using conventional methods, for example, HPLC.

As used herein, "acid-labile nitrogen protecting group" refers to a protecting group, on a nitrogen atom, that can be removed with acid to provide the —NH—. Such protecting groups are well known in the art. See, e.g., Greene, T. W., Wuts, P. G. M. *Greene's Protective Groups in Organic Synthesis*, John Wiley & Sons, Inc., 2007. Particularly preferred acid-labile nitrogen protecting groups include carboxyl-based protecting groups such as t-butyloxycarbonyl (Boc).

As used herein, "alkyl" refers to branched or unbranched, saturated hydrocarbons having from 1-30 carbons, preferably 1-6 carbons. Preferred alkyl groups include, for example, methyl, ethyl, propyl, isopropyl, butyl, sec-butyl, iso-butyl, tert-butyl, pentyl, isopentyl, and hexyl.

As used herein, "cycloalkyl" refers to cyclic, saturated hydrocarbons having from three to eight carbon atoms, preferably 3-6 carbons. Preferred cycloalkyl groups include, for example, cyclopropyl, cyclobutyl, cyclopentyl, cyclohexyl, and the like.

As used herein, OR⁴ is a leaving group, refers to groups subject to nucleophilic displacement by fluoride ions. Particularly preferred are those embodiments wherein OR⁴ is —Otosylate (—OTos, —OSO₂—C₆H₄—CH₃).

In preferred methods of the invention, the single diastereomers of the compounds of formula I are prepared by contacting a compound of formula IIIa or IIIb:

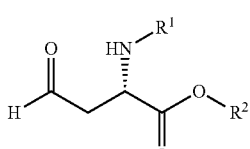

IIIa

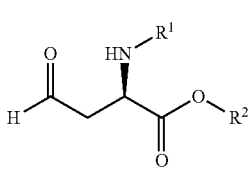

IIIb with a compound of formula IV

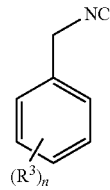

IV in the presence of chloroacetic acid to form a mixture of diastereomers of compounds of formula V.

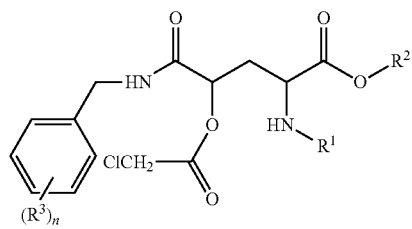

V

Those of skill in the art will readily understand that if the starting material is a compound of formula IIIa, the mixture diastereomers of the compound of formula V will preferably comprise compounds of formulas Va and Vb:

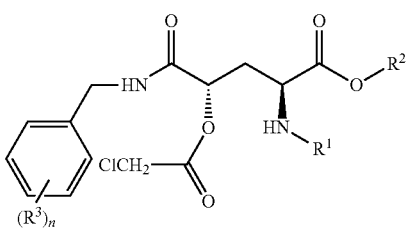

Va

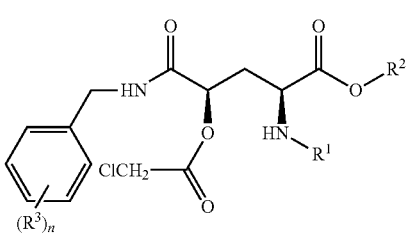

Vb

Similarly, if the starting material is a compound of formula IIIb, the mixture diastereomers of the compound of formula V will preferably comprise compounds of formulas Vc and Vd:

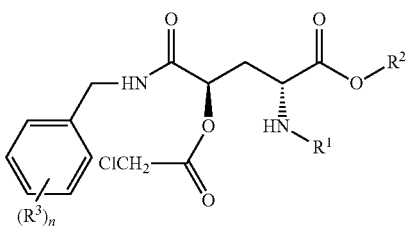

Vc

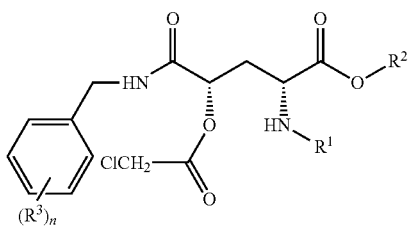
Vd

The mixture of diastereomers of compounds of formula V is reacted for a time and under conditions effective to form a mixture of diastereomers of compounds of formula VI:

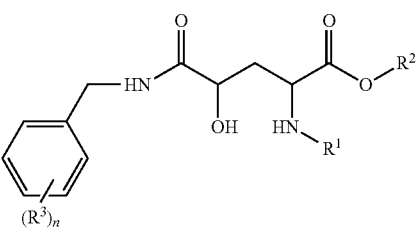
VI

Those of skill in the art will readily understand that if the mixture of diastereomers of compounds of formula V comprises compounds of formulas Va and Vb, then the mixture of diastereomers of compounds of formula VI will preferably comprise compounds of formulas VIa and VIb:

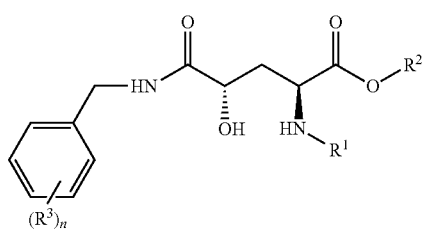
VIa

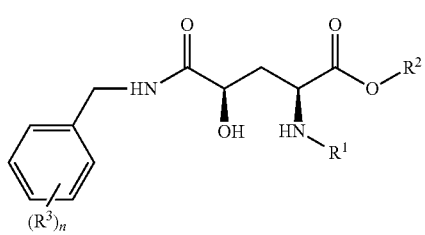
VIb

Similarly, if the mixture of diastereomers of compounds of formula V comprises compounds of formulas Vc and Vd, then the mixture of diastereomers of compounds of formula VI will preferably comprise compounds of formulas VIc and VId:

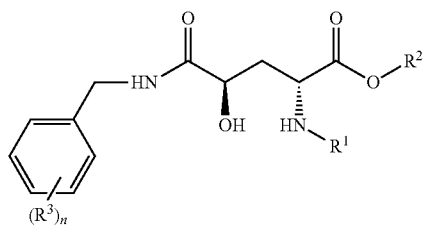
VIc

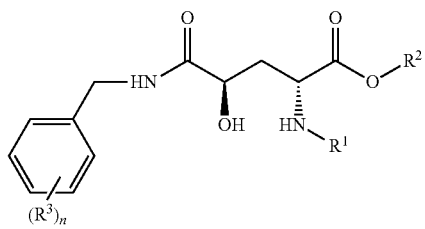
VId

In preferred embodiments, the mixture of diastereomers of the compound of formula VI is a mixture of compounds of formulas VIa and VIb:

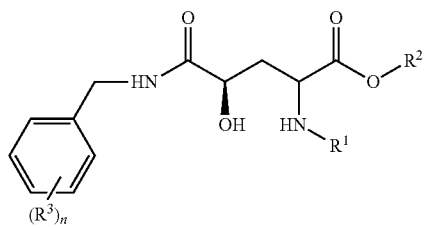
VIa

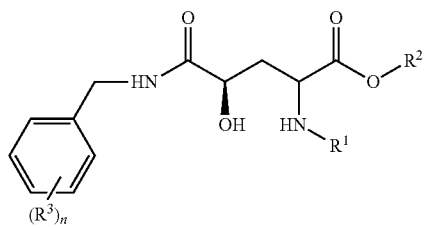
VIb

The mixture of diastereomers of the compounds of formula VI are then separated, preferably by physical separation. Methods of the physical separation of diastereomers are known in the art and include flash column chromatography and high performance liquid chromatography, for example. According to the invention, the mixtures of diastereomers of the compounds of formula VI are separated to provide single diastereomers of the compound of formula VI, having a diastereomeric excess of at least 80%, preferably having a diastereomeric excess of at least 90%, most preferably having a diastereomeric excess of at least 98%.

In preferred embodiments, $R^1$ is —C(O)O—$C_{1-6}$alkyl or —C(O)O—$C_{1-6}$cycloalkyl. In other embodiments, $R^1$ is —C(O)O—$C_{1-6}$alkyl. Preferably, $R^1$ is —C(O)O-t-butyl.

In other embodiments, $R^2$ is t-butyl. In still other embodiments $R^3$ is —OCH$_3$. In other embodiments, n is 3.

The single diastereomers of radiolabeled compounds of the invention, preferably labeled with $^{18}$F, can be formulated into compositions useful for diagnosing disease in a patient, in particular, cancer. While radiolabeled compounds 1, 2, 3, or 4 can be used in the diagnostic compositions of the invention, most preferred is the use of compounds 1 or 2 in the diagnostic compositions. These diagnostic compositions may be formulated for administration to a patient, for example by parenteral administration by injection, by formulating the composition with carriers and/or diluents known to those skilled in the art.

After administering a diagnostic composition of the invention to a patient, the gamma radiation from the single diastereomer can be detected as a means to image cancer in the patient. One exemplary method for such detection is positron emission topography (PET).

The following description is set forth as illustrative of the claimed invention and is not meant to be limiting.

2,4,6-Trimethoxybenzylisocyanide (Tmob-IC) was prepared from 2,4,6-trimethoxybenzylamine. See Scheme 4. After conversion to the corresponding formamide, treatment with triphosgene gave the desired isocyanide in 70% overall yield.

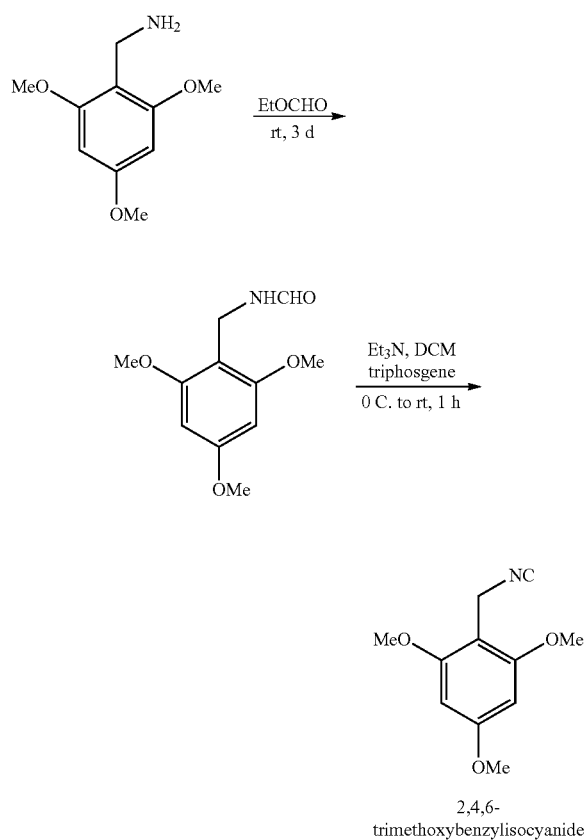

The preparation of aldehyde 8 is depicted in Scheme 5. Esterification of partially protected L-aspartic acid derivative A using tert-butyl trichloroacetimidate under the catalysis of BF$_3$ afforded 97% fully protected L-aspartic acid 5. After removal of the benzyl group by catalytic hydrogenation, a two-step combined reduction gave homoserine 6 in 87% overall yield. Subsequent oxidation with Dess-Martin periodinane reagent provided aldehyde 8 in 86% yield.

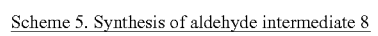
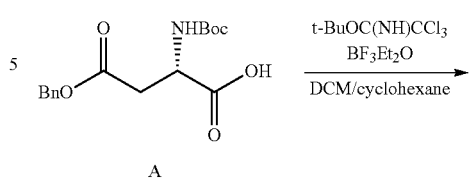
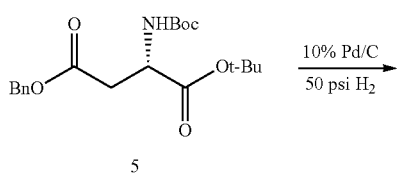
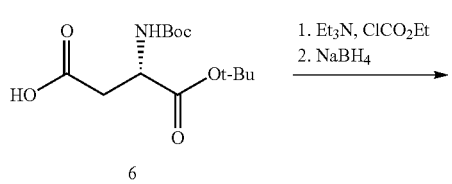
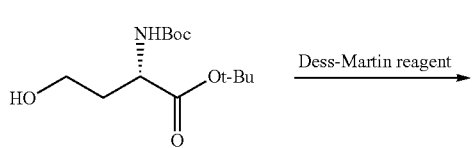
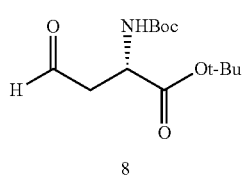

With both intermediates Tmob-IC and 8 prepared, a Passerini reaction was conducted to assemble the glutamine skeleton to provide 4-acyloxy substituted Gln derivative 9 in excellent yield.

Removal of the chloroacetyl group was effected using thiourea to produce compound 10. Scheme 6. The two diastereomeric isomers, alcohols 10' and 10" (1:1 ratio based upon HPLC analysis), show a clear polarity difference and can be separated by flash chromatography. Scheme 7. The absolute configurations of these two alcohols were determined by Mosher ester analysis. The assigned configurations are comparable with physical properties of both alcohols. The alcohol (10') with (2S,4R) configuration shows higher mp (143-145° C.), whereas, the alcohol (10") with (2S,4S) configuration shows a lower mp (58-61° C.). Tosylation of the hydroxyl afforded the tosylate 11 in 96% yield. Fluorination with hypervalent silicate fluorination agent, tris(dimethylamino) sulfonium difluorotrimethylsilicate (TASF) provided compound 12 (12' and 12") in 60-70% yield. Treatment with TFA produced the desired 4-fluoroglutamine (1 and 2).

Scheme 6. Synthesis of 4-fluoro-L-glutamine 13
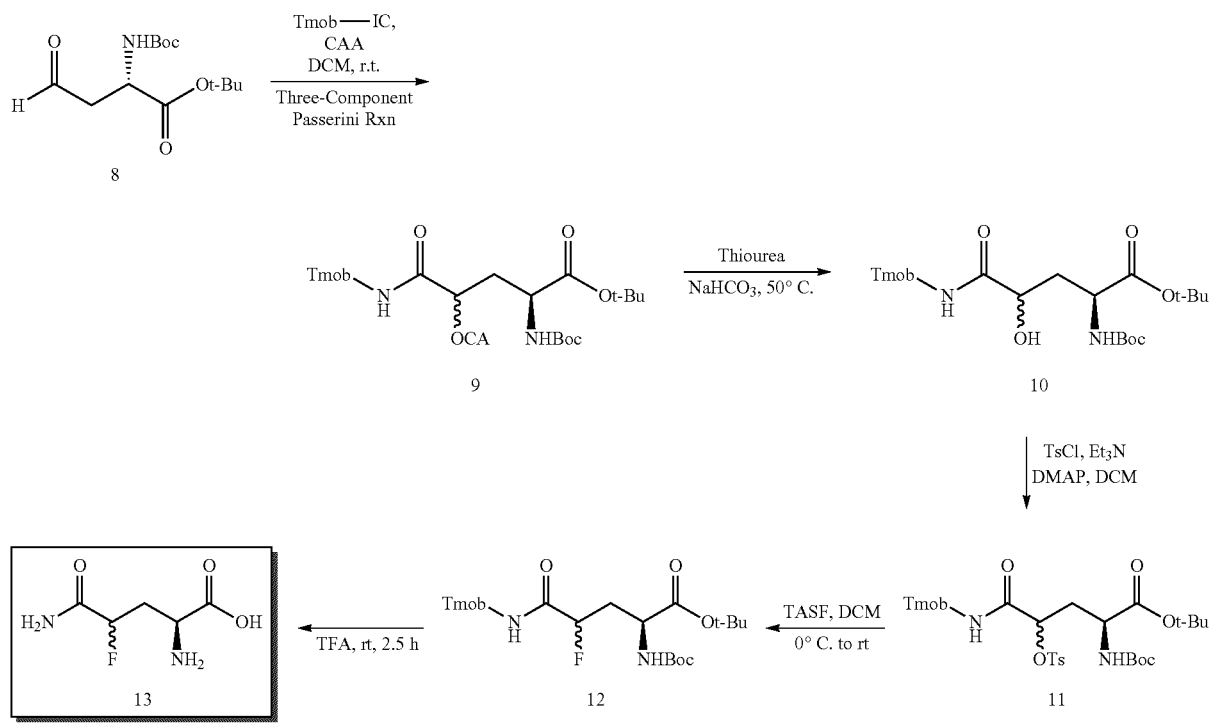
CAA: chloroacetic acid; CA: chloroacetyl
Tmob: 2,4,6-trimethoxybenzyl
Scheme 7. Synthesis of 4-fluoro-L-glutamines 1 and 2
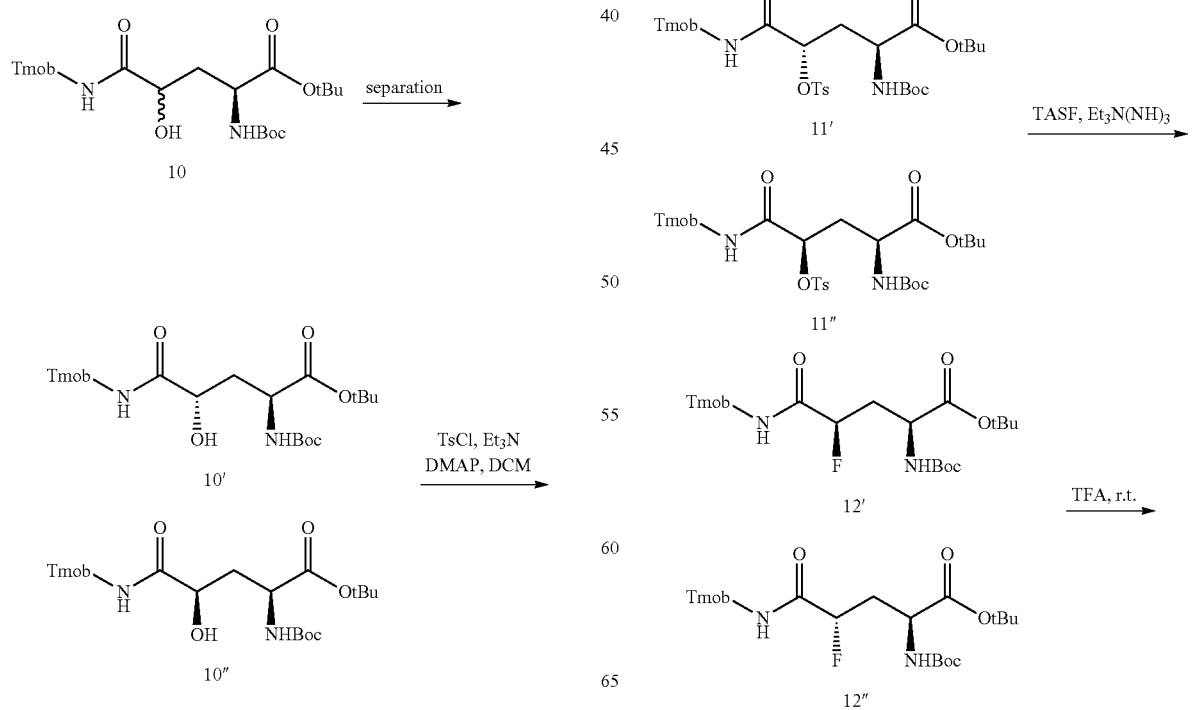

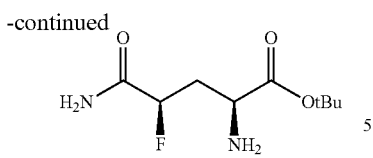

The preparation of the enantiomer of aldehyde 8, compound 8a, can be accomplished according to the sequence set forth in Scheme 8, starting from the commercially available D-aspartic acid derivative B.

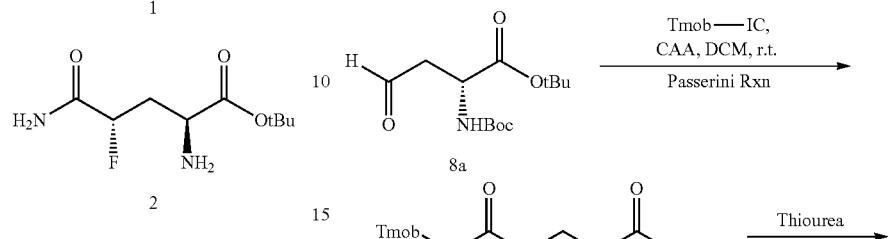

Next, aldehyde 8a was submitted to react with isocyanide and chloroacetic acid under the Passerini reaction conditions. The obtained intermediate 9a was subjected to de-acetylation using thiourea and NaHCO₃ combined conditions and following carefully flash chromatography separation afforded two stereospecific, 4-hydroxy group substituted D-glutamine derivatives 10a' and 10a". Scheme 9. The further transformations, including tosylation, fluorination and acidic deprotection reactions, afforded another two 4-FGln diastereomers, fluorinated D-glutamine analogs 3 and 4 with comparable yields. Again, slow evaporating method provided high quality crystal samples for both intermediates 10a', 12a' and final product 3. The X-ray crystallographic analysis further identified the absolute configurations of these compounds.

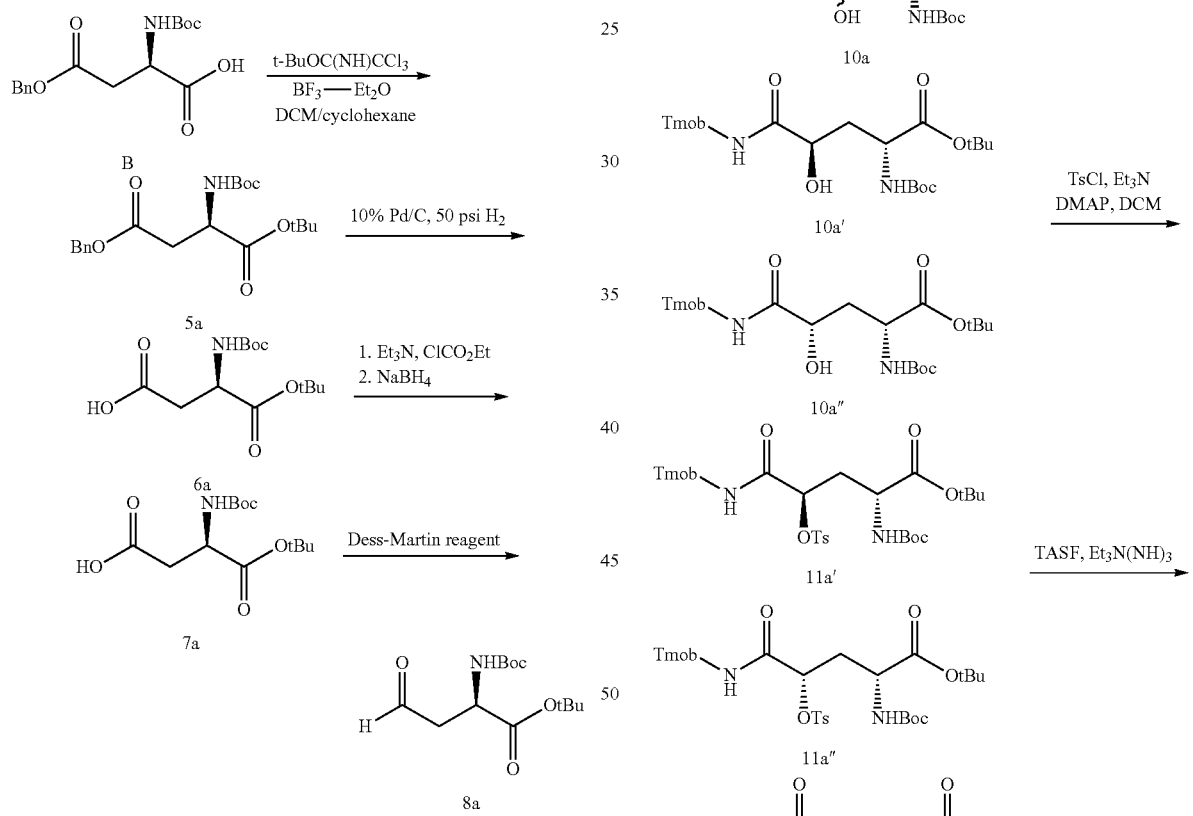

-continued

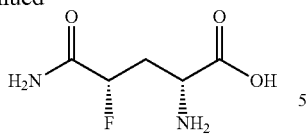
3

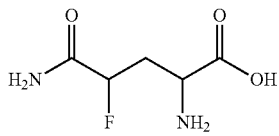
4

CAA: chloroacetic acid
CA: chloroacetyl
Tmob: 2,4,6-trimethoxybenzyl

Also within the scope of the invention are methods of preparing 4-fluoroglutamine

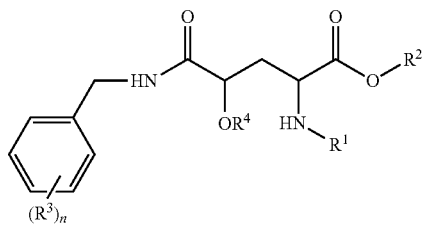
4-fluoro-glutamine comprising:
reacting a compound of formula I

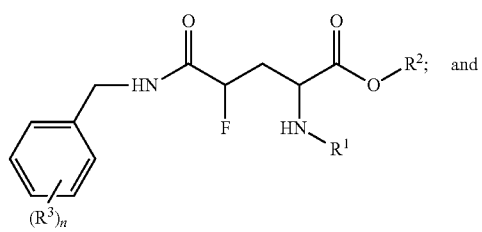
I wherein
$R^1$ is an acid-labile nitrogen protecting group;
$R^2$ is $C_{1-6}$alkyl;
each $R^3$ is independently —$OC_{1-6}$alkyl;
$OR^4$ is a leaving group; and
n is 0, 1, 2, 3, or 4;
with a fluorinating agent, for a time and under conditions effective to form a compound of formula II

II

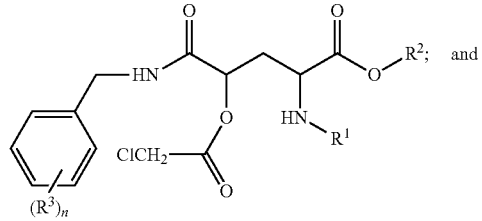

reacting the compound of formula II for a time and under conditions effective to produce the 4-fluoro-glutamine.

In preferred methods, the compound of formula I is prepared by contacting a compound of formula III

III

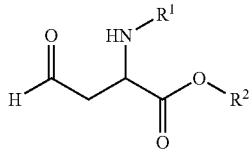

with a compound of formula IV

IV

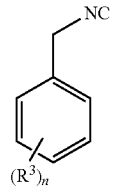

in the presence of chloroacetic acid to form a compound of formula V

V

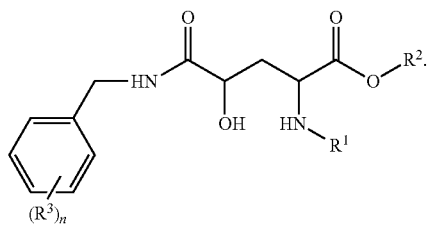

reacting the compound of formula V for a time and under conditions effective to form a compound of formula VI

VI

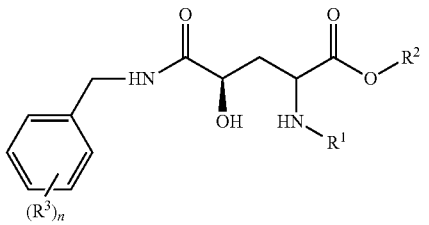

In certain embodiments, the compound of formula VI is a mixture of compounds of formula VIy and VIz:

VIy

-continued

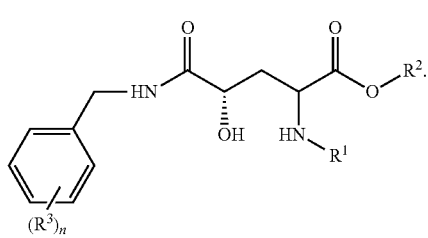

VIz

Preferably, the compounds of formulas VIy and VIz are physically separated. Preferred methods of physical separation include chromatography.

In preferred embodiments, $R^1$ is —C(O)O—$C_{1-6}$alkyl. More preferably, $R^1$ is —C(O)O-t-butyl. Also preferred is where $R^2$ is t-butyl. In some embodiments, $R^3$ is —$OCH_3$. In yet other embodiments, $OR^4$ is Otosylate. In still other embodiments, n is 3. A preferred fluorinating agent for use in the invention is tris(dimethylamino)sulfonium difluorotrimethylsilicate. Preferably, the fluorinating agent comprises $^{18}F$.

Preferably, the compound of formula III is

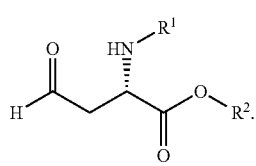

Preferably, the 4-fluoroglutamine is

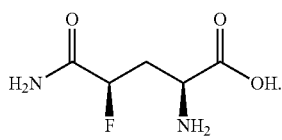

Also preferred is where the 4-fluoroglutamine is

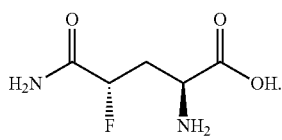

Also within the scope of the invention are compounds of the following formula I

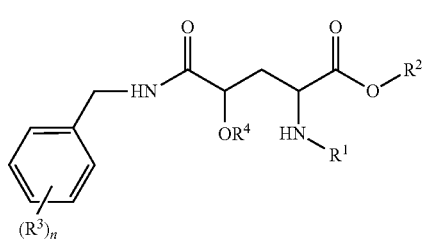

I wherein $R^1$ is an acid-labile nitrogen protecting group;

$R^2$ is $C_{1-6}$alkyl;

each $R^3$ is independently —$OC_{1-6}$alkyl;

$OR^4$ is a leaving group; and n is 0, 1, 2, 3, or 4.

Preferably, the compound of formula I is:

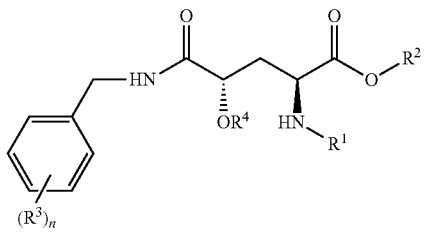

and

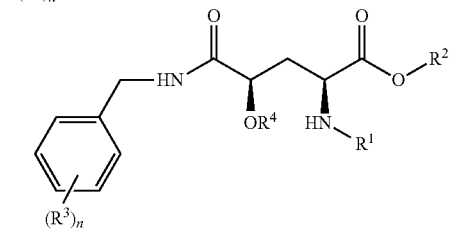

EXAMPLES

Those of skill in the art will readily understand that the following procedures are illustrative only, and are not intended to limit the scope of the invention. In addition, where procedures are set forth for one enantiomer or diastereomer or pair of diastereomers, similar procedures can be used to prepare the other enantiomer or diastereomers or pair of diastereomers.

General Information.

All reagents used were commercial products and were used without further purification unless otherwise indicated. Flash chromatography (FC) was performed using silica gel 60 (230-400 mesh, Sigma-Aldrich). For each procedure, "standard workup" refers to the following steps: pouring reaction mixture into the separatory funnel containing an equal volume of water, extracting this mixture with an equal volume of indicated organic solvent three times and combining the organic phases together, washing this organic layer with brine, drying it off with sodium sulfate or magnesium sulfate, filtering off the solid and concentrating the filtrate under reduced pressure. Melting points (mp) were checked on MEL-TEMP (uncorrected). $^1H$ NMR spectra were obtained at 200 MHz, $^{13}C$ NMR spectra were recorded at 50 MHz and $^{19}F$ NMR spectra were recorded at 282 MHz (Bruker DPX 200 and DMX 300 spectrometers). Chemical shifts are reported as δ values (parts per million) relative to remaining protons in deuterated solvent. Coupling constants are reported in hertz. The multiplicity is defined by s (singlet), d (doublet), t (triplet), q (quartet), p (pentet), br (broad) or m (multiplet). HPLC analyses were performed on an Aglient LC 1100 series. High-resolution MS experiments were performed at Radiopharmaceutical Chemistry Section, Department of Radiology, University of Pennsylvania, using an Agilent Technologies LC/MSD TOF Mass Spectrometer. Optical rotation values were measured on a Perkin Elmer Model 243B polarimeter.

2-(isocyanomethyl)-1,3,5-trimethoxybenzene
Tmob-IC N-(2,4,6-trimethoxybenzyl)formamide

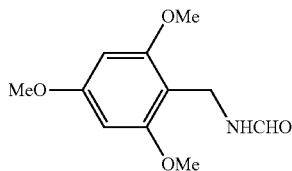

Ethyl formate (7.5 mL, 93 mmol) was added to a 25 mL round bottom flask containing 2,4,6-trimethoxybenzylamine (0.985 g, 5.0 mmol). The reaction mixture was stirred at room temperature for three days and was filtered. The filtered out white solid was collected and dried under vacuum to provide crude product (1.09 g, 97%): $^1$H NMR (200 MHz, CDCl$_3$) δ 8.19 (s, 0.3H), 8.14 (s, 0.7H), 6.13 (d, 2H, J$_2$=3.0 Hz), 6.00 (br s, 1H), 4.51 (d, 1H, J=5.2 Hz), 4.35 (d, 1H, J=6.4 Hz), 3.83 (s, 3H), 3.82 (s, 6H).

Ref: F. Christopher Pigge, John J. Coniglio, Shiyue Fang. *Organometallics* 2002, 21, 4504-4512

2-(isocyanomethyl)-1,3,5-trimethoxybenzene

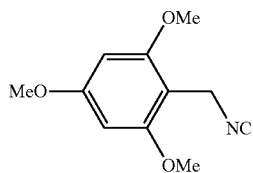

To a stirred solution of the previously prepared fomamide (0.675 g, 3.0 mmol) and triethyl amine (1 mL) in 5 mL CH$_2$Cl$_2$ cooled in an ice bath was added triphosgene solution (0.356 g, 1.2 mmol dissolved in 5 mL CH$_2$Cl$_2$) dropwise. After addition and exothermic phenomena faded, the reaction mixture was set-aside at room temperature and samples were collected for TLC. When the reactant formamide had been consumed, the reaction mixture was submitted to standard workup with CH$_2$Cl$_2$. Crude product was purified by flash column chromatography (FC) (20%-25% EtOAc in hexanes as solvent) to provide light yellow crystalline solid product (0.435 g, 70%): mp 107-109° C.; $^1$H NMR (200 MHz, CDCl$_3$) δ 6.13 (s, 1H), 4.55 (t, 2H, J=1.7 Hz), 3.86 (s, 6H), 3.83 (s, 3H); $^{13}$C NMR (50 MHz, CDCl$_3$) δ 162.2, 159.2, 153.18, 153.08, 152.98, 102.6, 90.6, 55.9, 55.5, 34.3, 34.1, 34.0; HRMS calcd for C$_{11}$H$_{11}$NO$_3$ (M+H)$^+$: 208.0974. found: 208.0961; C$_{11}$H$_{13}$NaNO$_3$ (M+Na)$^+$: 230.0793. found: 230.0778.

Ref: Susana P. G. Costa, Hemani L. S. Maia, Silvia M. M. A. Pereira-Lima. *Org. Biomol. Chem.* 2003, 1, 1475-1479

Intermediate (S)-4-tert-butyl-2-(tert-butoxycarbonylamino)-4-oxobutanoate (8) (S)-4-benzyl 1-tert-butyl 2-(tert-butoxycarbonylamino)succinate (5)

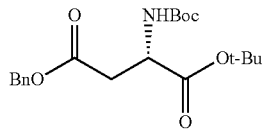 [SMILES: CC(C)(C)OC(=O)N[C@@H](CC(=O)OCc1ccccc1)C(=O)OC(C)(C)C]

Compound A (0.969 g, 3.0 mmol) was dissolved in 10 mL CH$_2$Cl$_2$ in a 50 mL round bottom flask. To this solution tert-butyl 2,2,2-trichloroacetamidate (1.31 g, 6 mmol) and BF$_3$.Et$_2$O (37 μL, 0.3 mmol) were added. After stirring at room temperature for 2 h, the reaction mixture was cooled in an ice bath and solid NaHCO$_3$ (0.84 g, 10 mmol) was added in one portion. This mixture was stirred for 10 min and filtered over a silica plug. The filtrate was evaporated in vacuo and the residue was purified by FC (EtOAc/Hexanes, 15/85, vol/vol) to provide a white solid 5 (1.10 g, 97%): mp 63-64° C. (lit.$^1$ 64-65° C.; lit.$^2$ 61-63° C.); [α]$^{24}$$_D$=+20.0 (c=1.0, CHCl$_3$) and [α]$^{24}$$_D$=−8.1 (c=2.0, MeOH) [lit$^2$ [α]$^{22}$$_D$=+19.6 (c=1.0, CHCl$_3$); lit$^3$ [α]$^{25}$$_D$=−7.4 (c=2.0, MeOH)]; $^1$H NMR (200 MHz, CDCl$_3$) δ 7.35 (s, 5H), 5.45 (d, 1H, J=8.0 Hz), 5.13 (d, 2H, J=2.6 Hz), 4.46 (pentet, 1H, J=4.4 Hz), 3.00 (dd, 1H, J$_1$=16.8 Hz, J$_2$=4.6 Hz), 2.83 (dd, 1H, J$_1$=16.8 Hz, J$_2$=4.8 Hz), 1.45 (s, 9H), 1.42 (s, 9H); $^{13}$C NMR (50 MHz, CDCl$_3$) δ 170.6, 169.8, 155.3, 135.6, 128.4, 128.2, 82.0, 79.6, 66.4, 50.6, 37.0, 28.2, 27.7;

HRMS calcd for C$_{20}$H$_{29}$NaNO$_6$ (M+Na)$^+$: 402.1893. found: 402.1886.

Ref: for tert-butyl esterification: A. Armstrong, I. Brackenridge, R. F. W. Jackson, J. M. Kirk. *Tetrahedron Lett.* 1988, 29, 2483-2486

For the product identification (melting point and optical rotation):

1. Stephen C. Bergmeir, Agustin A. Cobas, Henry Rapoport. *The Journal of Organic Chemistry* 1993, 58, 2369-2376
2. Robert M. Adlington, Jack E. Baldwin, David Catterick, Gareth J. Pareth J. Pritchard. *J. Chem. Soc., Perkin Trans.* 1, 1999, 855-866
3. Madhup K. Dhaon, Richard K. Olsen, K. Ramasamy. *The Journal of Organic Chemistry* 1982, 47, 1962-1965

(S)-4-tert-butoxy-3-(tert-butoxycarbonylamino)-4-oxobutanoic acid (6)

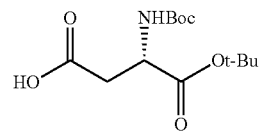 [SMILES: CC(C)(C)OC(=O)N[C@@H](CC(=O)O)C(=O)OC(C)(C)C]

A mixture of the ester 5 (1.04 g, 2.74 mmol) and 10% Pd/C (0.2 g) in absolute EtOH (20 mL) was shaken with hydrogen at 50 psi for 3 h. This mixture was then filtered and the filtrate was concentrated under vacuum to give a white crystalline solid 6 (0.79 g, 100%): mp 97-99° C. (lit.$^1$ 97-98° C.; lit.$^2$ 98-100° C.); [α]$^{24}$$_D$=−16.9 (c=1.0, EtOH) and [α]$^{23.5}$$_D$=−

23.6 (c=1.5, MeOH) [lit[2] [α]$^{22}_D$=+19.6 (c=1.0, CHCl$_3$); lit[3] [α]$^{25}_D$=−7.4 (c=2.0, MeOH)]; $^1$H NMR (200 MHz, CDCl$_3$) δ 10.33 (br s, 1H), 5.48 (d, 1H, J=8.0 Hz), 4.45 (t, 1H, J=4.0 Hz), 3.02 (dd, 1 H, J$_1$=17.0 Hz, J$_2$=4.0 Hz), 2.81 (dd, 1H, J$_1$=17.2 Hz, J$_2$=4.6 Hz), 1.45 (br s, 18H); $^{13}$C NMR (50 MHz, CDCl$_3$) δ 175.8, 169.9, 155.7, 82.4, 80.2, 50.5, 36.8, 28.3, 27.9; FIRMS calcd for C$_{13}$H$_{23}$NaNO$_6$ (M+Na)$^+$: 312.1423. found: 312.1420.

Ref: 1. C. C. Yang, R. B. Merrifield. *The Journal of Organic Chemistry* 1976, 41, 1032-1041 2. Robert M. Adlington, Jack E. Baldwin, David Catterick, Gareth J. Pareth J. Pritchard. *J. Chem. Soc., Perkin Trans.* 1, 1999, 855-866

(S)-4-tert-butyl-2-(tert-butoxycarbonylamino)-4-hydroxybutanoate (7)

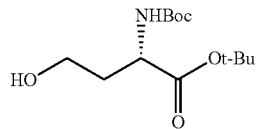 [SMILES: CC(C)(C)OC(=O)N[C@@H](CCO)C(=O)OC(C)(C)C]

Acid 6 (0.733 g, 2.54 mmol) was dissolved in 5 mL THF in a 50 mL round bottom flask and the solution was cooled to −10° C. To this solution Et$_3$N (0.39 mL, 2.79 mmol) and ethyl chloroformate (0.27 mL, 2.79 mmol) were added dropwise. After stirring −10 to −5° C. for 30 min, the reaction mixture was filtered off. To a mixture of NaBH$_4$ (0.203 g, 5.33 mmol) with 2 mL H$_2$O in a 100 mL two-neck flask cooled with an ice bath was added above filtrate slowly. The mixture was stirred at room temperature for further 4 h and was then acidified with 1M HCl until the PH=2-3 under the cooling with ice bath. The organic phase was collected and water phase was extracted with EtOAc (20 mL×3). The organic phases were combined, washed with Sat. NaHCO$_3$ (20 mL) and brine (20 mL), and dried with MgSO$_4$. The filtrate was evaporated in vacuo and the residue was purified by FC (EtOAc/Hexanes, 35/65 to 45/55, vol/vol) to provide 7 (0.618 g, 87%): [α]$^{25}_D$=−39.9 (c=1.0, EtOH) [lit [α]$^{25}_D$=−37.5 (c=1.0, EtOH)]; $^1$H NMR (200 MHz, CDCl$_3$) δ 5.35 (br s, 1H), 4.36 (br s, 1H), 3.77-3.57 (m, 2H), 2.92 (br s, 1H), 2.20-2.05 (m, 2H), 1.48 (s, 9H), 1.45 (s, 9H); $^{13}$C NMR (50 MHz, CDCl$_3$) δ 172.1, 156.6, 82.3, 80.3, 58.5, 51.3, 36.44, 28.4, 28.1; HRMS calcd for C$_{13}$H$_{25}$NaNO$_5$ (M+Na)$^+$: 298.1630. found: 298.1632.

Ref: K. Ramsamy, Richard K. Olsen, Thomas Emary. *Synthesis*, 1982, 42-43

(S)-4-tert-butyl-2-(tert-butoxycarbonylamino)-4-oxobutanoate (8)

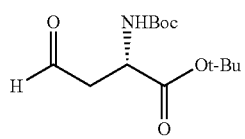 [SMILES: CC(C)(C)OC(=O)N[C@@H](CC=O)C(=O)OC(C)(C)C]

To a solution of alcohol 7 (0.284 g, 1.03 mmol) in CH$_2$Cl$_2$ (5 mL) was added solid NaHCO$_3$ (0.861 g, 10.25 mmol) and Dess-Martin periodinane reagent (5.1 mL 0.3 M CH$_2$Cl$_2$ solution, 1.53 mmol). The solution was stirred at room temperature for 1 h. Sodium thiosulfate solution (1.0M, 5 mL) was added and the resulting biphasic mixture was vigorously stirred for 5 min and saturated NaHCO$_3$ (5 mL) was then added. The mixture was then extracted with CH$_2$Cl$_2$ (15 mL×3). The combined organic layers were dried over MgSO$_4$, filtered, and concentrated in vacuo to afford crude product. Flash chromatography (EtOAc/Hexanes, 20/80, V/V) furnished aldehyde 8 (0.243 g, 86%) as a white crystalline solid: mp 61.5-63° C. (lit.[1] 60-62° C.; lit.[2] 66-67° C.); [α]$^{23.5}_D$=+18.6 (c=1.95, CH$_2$Cl$_2$) and [α]$^{25}_D$=−26.1 (c=1.5, absolute EtOH) [lit.[1] [α]$^{21}_D$=+20.7 (c=1.95, CH$_2$Cl$_2$); lit[3] [α]$^{25}_D$=−21.6 (c=1.5, EtOH)]; $^1$H NMR (200 MHz, CDCl$_3$) δ 9.73 (s, 1H), 5.35 (d, 1H, J=6 Hz), 4.47 (m, 1H), 2.97 (t, 2H, J=4.4 Hz), 1.45 (s, 9H), 1.44 (s, 9H); $^{13}$C NMR (50 MHz, CDCl$_3$) δ 199.4, 170.1, 155.5, 82.8, 80.2, 49.6, 46.5, 28.4, 28.0; HRMS calcd for C$_{13}$H$_{23}$NaNO$_5$ (M+Na)$^+$: 296.1474. found: 286.1469.

Ref: for D-M reagent oxidation: D. B. Dess, J. C. Martin. *The Journal of Organic Chemistry* 1983, 48, 4155-4156

For the product identification (mp and optical rotation):

1. R. Marshall Werner, On Shokek, Jeffery T. Davis. *The Journal of Organic Chemistry* 1997, 62, 8243-8246
2. Domink Werinik, John Dimaio, Julian Adams. *The Journal of Organic Chemistry* 1989, 54, 4224-4228
3. K. Ramsamy, Richard K. Olsen, Thomas Emary. *Synthesis*, 1982, 42-43

(2S)-tert-butyl 2-(tert-butoxycarbonylamino)-4-(2-chloroacetoxy)-5-oxo-5-(2,4,6-trimethoxybenzylamino)pentanoate (9)

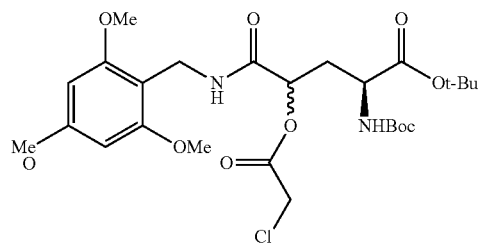 [SMILES: COc1cc(OC)c(CNC(=O)C(C[C@H](NC(=O)OC(C)(C)C)C(=O)OC(C)(C)C)OC(=O)CCl)c(OC)c1]

To a stirred solution of 8 (0.366 g, 1.33 mmol) in CH$_2$Cl$_2$ (10 mL) was added 2-(isocyanomethyl)-1,3,5-trimethoxybenzene (0.303 g, 1.46 mmol) and chloroacetic acid (0.138 g, 1.46 mmol). The reaction was stirred at room temperature for 24 h. The solvent was removed under vacuum and the residue was chromatographed on silica gel (EtOAc/Hexanes, 30/70 to 40/60, V/V) to give 9 as a waxy white solid (0.727 g, 95%): $^1$H NMR (200 MHz, CDCl$_3$) δ 6.79 (br s, 0.5H), 6.48 (t, 0.5H, J=5.1 Hz), 5.26-5.03 (m, 2H), 4.65-4.22 (m, 3H), 4.13 (d, 2H, J=13.4 Hz), 3.81 (s, 9H), 2.51-2.05 (m, 2H), 1.46 (s, 9H), 1.42 (d, 9H, J=5.8 Hz). $^{13}$C NMR (50 MHz, CDCl$_3$) δ 171.1, 171.0, 168.0, 167.6, 166.4, 166.2, 161.2, 159.4, 155.5, 106.3, 106.1, 90.8, 82.6, 82.5, 80.2, 72.5, 71.9, 55.9, 55.5, 51.1, 50.5, 40.9, 40.7, 34.9, 34.7, 32.5, 28.4, 28.1.

HRMS calcd for C$_{26}$H$_{40}$ClN$_2$O$_{10}$ (M+H)$^+$: 575.2371. found: 575.2360.

Ref: for Passerini reaction: Alexander Domling. *Chem. Rev.* 2006, 106, 17-89 and reference therein

(2S)-tert-butyl 2-(tert-butoxycarbonylamino)-4-hydroxy-5-oxo-5-(2,4,6-trimethoxybenzyl amino)pentanoate (10)

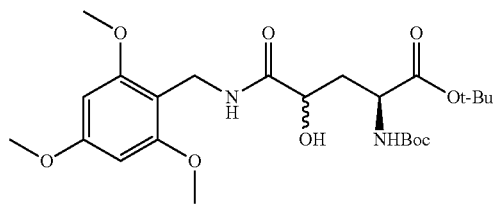 [SMILES: COc1cc(OC)c(CNC(=O)C(O)C[C@H](NC(=O)OC(C)(C)C)C(=O)OC(C)(C)C)c(OC)c1]

To a stirred solution of 9 (0.678 g, 1.18 mmol) in EtOH/THF (5/5 mL) was added thiourea (0.269 g, 3.54 mmol) and NaHCO$_3$ (0.297 g, 3.54 mmol). The reaction mixture was stirred and heated to 50° C. for 1.5 h. The solvent was then removed under the reduced pressure and the residue was submitted to FC on silica gel (EtOAc/Hexanes, 45/55 to 60/40, V/V) to give 10 as a mixture of C(4) diastereomers as a waxy white solid (0.543 g, 91%): $^1$H NMR (200 MHz, CDCl$_3$) δ 7.26 (br s, 1H), 6.13 (s, 1H), 6.12 (s, 1H), 5.45 (d, 1H, J=5.6 Hz), 4.63-4.03 (m, 5H), 3.82, 3.81 (s, s, total 9H), 2.43-1.84 (m, 2H), 1.45 (d, 9H, J=1.2 Hz), 1.43 (s, 9H); $^{13}$C NMR (50 MHz, CDCl$_3$) δ 172.6, 172.0, 171.5, 171.3, 161.0, 159.5, 157.3, 156.1, 106.7, 90.8, 82.7, 82.4, 80.8, 80.3, 69.6, 68.5, 55.9, 55.4, 52.0, 51.0, 39.1, 38.5, 32.2, 31.9, 28.3, 28.0; HRMS calcd for C$_{24}$H$_{39}$N$_2$O$_9$ (M+H)$^+$: 499.2656. found: 499.2669, 499.2662.

Ref: 1. Mitsuo Masaki, Takeshi Kitahara, Hideaki Kurita, Masaki Ohta. *Journal of the American Chemical Society* 1968, 90, 4508-4509

2. M. Naruto, K. Ohno, N. Naruse, and H. Takeuchi. *Tetrahedron Lett.* 1979, 251

(2S,4S)-tert-butyl 2-(tert-butoxycarbonylamino)-4-hydroxy-5-oxo-5-(2,4,6-trimethoxy benzylamino) pentanoate (10') and (2S,4R)-tert-butyl 2-(tert-butoxycarbonylamino)-4-hydroxy-5-oxo-5-(2,4,6-trimethoxybenzylamino)pentanoate (10")

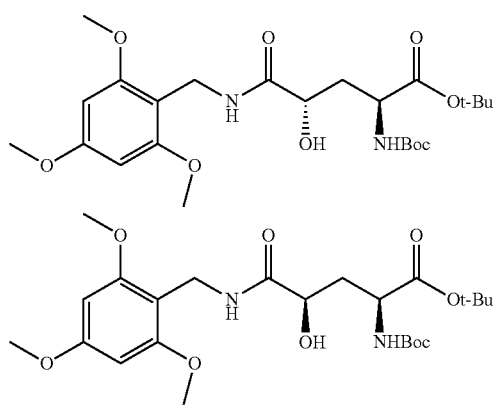

The two diastereomers' mixture 10 obtained above was submitted to FC (silica gel 60, EtOAc/Hexanes, 30/70 to 60/40, V/V) to present two diastereomers—alcohol 10' and 10". Alcohol 10': white solid: mp 143-145° C.; [α]$^{26}_D$=−28.7 (c=1.06, MeOH); HPLC of 10': >99% [Rt=9.45 min; column: Lux 3u Cellulose-1 (150×4.6 mm) tandem connected with Chiralcel OD (250×4.6 mm), UV detector, 210 nm, 15% 2-propanol in hexanes; flow rate: 1.0 mL/min]. $^1$H NMR (200 MHz, CDCl$_3$) δ 7.23 (br s, 1H), 6.09 (s, 2H), 5.47 (d, 1H, J=7.6 Hz), 4.89 (d, 1H, J=4.2 Hz), 4.54-4.22 (m, 2H), 4.03 (dt, 1H, J$_1$=11.8 Hz, J$_2$=3.6 Hz), 3.78 (s, 6 H), 3.77 (s, 3H), 2.27-1.86 (m, 2H), 1.42 (s, 9H), 1.39 (s, 9H). $^{13}$C NMR (50 MHz, CDCl$_3$) 171.9, 171.3, 161.0, 159.5, 157.3, 106.8, 90.8, 82.6, 80.7, 68.5, 55.9, 55.4, 51.0, 39.1, 31.9, 28.3, 28.0. HRMS calcd for C$_{24}$H$_{39}$N$_2$O$_9$ (M+H)$^+$: 499.2656. found: 499.2643.

Alcohol 10": white solid: mp 58-61° C.; [α]$^{26}_D$=+10.5 (c=1.0, MeOH); HPLC of 10": >99%. [Rt=9.36 min; column: Lux 3u Cellulose-1 (150×4.6 mm) tandem connected with Chiralcel OD (250×4.6 mm), UV detector, 210 nm, 15% 2-propanol in hexanes; flow rate: 1.0 mL/min].

$^1$H NMR (200 MHz, CDCl$_3$) δ 7.24 (br s, 1H), 6.12 (s, 2H), 5.42 (d, 1H, J=7.0 Hz), 4.89 (d, 1 H, J=4.2 Hz), 4.58 (dd, 1H, J$_1$=13.6 Hz, J$_2$=5.8 Hz), 4.39 (dd, 1H, J$_1$=13.6 Hz, J$_2$=5.0 Hz), 4.26-4.11 (m, 2H), 4.02 (br s, 1H), 3.814 (s, 6H), 3.808 (s, 3H), 2.36 (dt, 1H, J$_1$=14.4 Hz, J$_2$=5.0 Hz), 1.91 (dt, 1H, J$_1$=14.4 Hz, J$_2$=7.6 Hz), 1.46 (s, 9H), 1.43 (s, 9H). $^{13}$C NMR (50 MHz, CDCl$_3$) δ 172.5, 171.6, 161.1, 159.6, 156.3, 106.9, 90.9, 82.6, 80.4, 69.8, 56.0, 55.5, 52.2, 38.7, 32.3, 28.4, 28.1. HRMS calcd for C$_{24}$H$_{39}$N$_2$O$_9$ (M+H)$^+$: 499.2656. found: 499.2638.

(2S)-tert-butyl-2-(tert-butoxycarbonylamino)-5-oxo-4-(tosyloxy)-5-(2,4,6-trimethoxybenzyl amino)pentanoate (11)

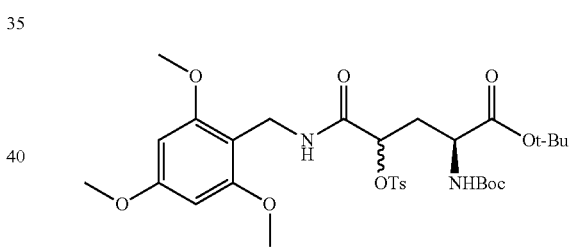

To a stirred solution of 10 (0.546 g, 1.09 mmol) in CH$_2$Cl$_2$ (10 mL) cooled with ice bath (0° C.) was added Et$_3$N (0.76 mL, 5.45 mmol), p-toluenesulfonyl chloride (TsCl, 0.416 g, 2.18 mmol) and catalytic amount 4-dimethylaminopyridine (DMAP, 0.11 mmol, 0.013 g). After maintaining at 0° C. for 15 min., the ice bath was removed, the reaction kept at r.t. overnight and then submitted to standard workup with CH$_2$Cl$_2$. The crude product was purified by FC (EtOAc/Hexanes, 40/60 to 50/50, V/V) to provide a pale white solid 11 (0.68 g, 96%). HPLC of 11: isomer one: 50%, Rt=12.53 min; isomer two: 50%, Rt=18.72 min; [column: Lux 3u Cellulose-1 (150×4.6 mm), UV detector, 210 nm, 5% 2-propanol in hexanes; flow rate: 1.0 mL/min]. $^1$HNMR (200 MHz, CD$_2$Cl$_2$) δ 7.72 (d, 2H, J=8.2 Hz), 7.28 (d, 2H, J=8.2 Hz), 6.79 (d, 1H, J=20.6 Hz), 6.15 (s, 2H), 5.14 (br s, 1H), 4.83 (t, 1H, J=6.8 Hz), 4.50-3.94 (m, 3H), 3.82 (s, 6H), 3.81 (s, 3H), 2.41 (s, 3H), 2.28-2.11 (m, 2H), 1.43 (s, 9H), 1.42 (s, 9H). $^{13}$C NMR (50 MHz, CD$_2$Cl$_2$) δ 171.0, 167.3, 161.8, 159.9, 155.8, 146.3, 133.3, 130.6, 128.5, 128.4, 106.6, 106.4, 91.3, 82.8, 82.5, 80.2, 78.0, 77.7, 56.4, 56.0, 35.7, 35.3, 32.9, 28.7, 28.3, 22.0. HRMS calcd for C$_{31}$H$_{45}$N$_2$O$_{11}$S (M+H)$^+$: 653.2744. found: 653.2734, 653.2739.

(2S,4R)-tert-butyl-2-(tert-butoxycarbonylamino)-5-oxo-4-(tosyloxy)-5-(2,4,6-tri methoxybenzylamino) pentanoate (11')

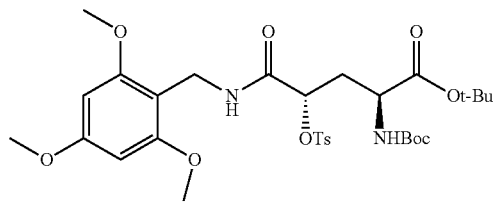 [SMILES: COc1cc(OC)c(CNC(=O)[C@H](C[C@H](NC(=O)OC(C)(C)C)C(=O)OC(C)(C)C)OS(=O)(=O)c2ccc(C)cc2)c(OC)c1]

Following the procedure in the preparation of 11, compound 11' was prepared from alcohol 10' (2.010 g, 4.04 mmol) as a pale white foamy solid (2.599 g, 99% yield): $[\alpha]^{26}_D = -30.5$ (c=1.04, MeOH); HPLC of 11' for purity: 98.0%, [major peak: Rt=15.9 min; minor peaks: 19.0 min and 24.6 min; column: Chiralcel ODH (250×4.6 mm), UV detector, 210 nm, 5% 2-propanol in hexanes; flow rate: 1.0 mL/min]. $^1$HNMR (200 MHz, CD$_2$Cl$_2$) δ 7.72 (d, 2H, J=8.4 Hz), 7.28 (d, 2H, J=8.2 Hz), 6.73 (br s, 1H), 6.15 (s, 2H), 5.12 (br s, 1H), 4.84 (t, 1H, J=6.0 Hz), 4.39 (dd, 1H, J$_1$=13.9 Hz, J$_2$=5.7 Hz), 4.27 (dd, 1H, J$_1$=13.9 Hz, J$_2$=5.3 Hz), 3.96 (q, 1H, J=7.4 Hz), 3.821 (s, 3H), 3.817 (s, 6H), 2.41 (s, 3H), 2.20 (t, 2H, J=6.4 Hz), 1.43 (s, 9H), 1.42 (s, 9H). $^{13}$C NMR (50 MHz, CD$_2$Cl$_2$) δ 170.6, 167.1, 161.2, 159.4, 155.4, 145.5, 132.9, 130.1, 128.1, 106.1, 90.9, 82.1, 79.9, 77.5, 56.0, 55.5, 51.6, 34.8, 32.6, 28.4, 28.1, 21.8. HRMS calcd for C$_{31}$H$_{45}$N$_2$O$_{11}$S (M+H)$^+$: 653.2744. found: 653.2740.

(2S,4S)-tert-butyl-2-(tert-butoxycarbonylamino)-5-oxo-4-(tosyloxy)-5-(2,4,6-tri methoxybenzylamino) pentanoate (11")

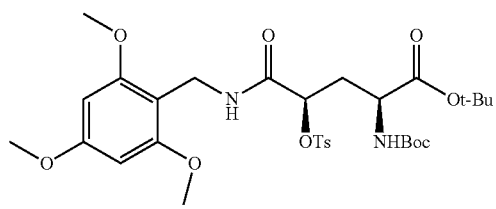 [SMILES: COc1cc(OC)c(CNC(=O)[C@@H](C[C@H](NC(=O)OC(C)(C)C)C(=O)OC(C)(C)C)OS(=O)(=O)c2ccc(C)cc2)c(OC)c1]

Following the procedure in the preparation of 11, compound 11" was prepared from alcohol 10" (1.69 g, 3.40 mmol) as a pale white foamy solid (2.12 g, 96% yield): $[\alpha]^{26}_D = +14.1$ (c=1.01, MeOH); HPLC of 11" for purity: 97.7%, [major peak: Rt=23.7 min; minor peak: 16.2 min; column: Chiralcel ODH (250×4.6 mm), UV detector, 210 nm, 5% 2-propanol in hexanes; flow rate: 1.0 mL/min]. $^1$H NMR (200 MHz, CDCl$_3$) δ 7.75 (d, 2H, J=8.4 Hz), 7.25 (d, 2H, J=8.4 Hz), 6.91 (br s, 1H), 6.14 (s, 2H), 5.12 (br s, 1H), 4.94 (t, 1H, J=6.0 Hz), 4.52 (dd, 1H, J$_1$=14.0 Hz, J$_2$=6.0 Hz), 4.30 (dd, 1H,//=14.4 Hz, J$_2$=5.2 Hz), 4.18 (br s, 1H), 3.84 (s, 3H), 3.82 (s, 6H), 2.42 (s, 3H), 2.32-2.22 (m, 2H), 1.45 (s, 9H), 1.43 (s, 9H). $^{13}$C NMR (50 MHz, CDCl$_3$) δ 170.7, 167.1, 161.2, 159.5, 155.5, 145.5, 133.1, 130.1, 128.2, 106.3, 90.9, 82.4, 79.9, 56.0, 55.6, 50.8, 35.0, 32.7, 28.5, 28.1, 21.8. HRMS calcd for C$_{31}$H$_{45}$N$_2$O$_{11}$S (M+H)$^+$: 653.2744. found: 653.2729.

Procedure for fluorination by TASF: synthesis of tert-butyl-2-(tert-butoxycarbonylamino)-4-fluoro5-oxo-5-(2,4,6-trimethoxybenzyl amino)pentanoate (12)

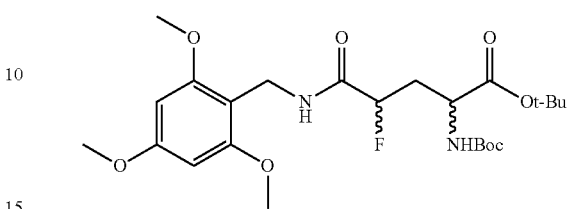

To a stirred solution of 11 (0.340 g, 0.52 mmol) in CH$_2$Cl$_2$ (7 mL) cooled in an ice bath (0° C.) tris(dimethylamino)sulfonium difluorotrimethylsilicate (TASF, 0.287 g, 1.04 mmol) dissolved in CH$_2$Cl$_2$ (3 mL) was added dropwise. After maintaining at 0° C. for 1 h., the ice bath was removed, the reaction was kept at r.t. for 12 h. The second part of the TASF reagent (0.287 g, 1.04 mmol dissolved in 1 mL of CH$_2$Cl$_2$) was added and the reaction was kept at r.t. for another 12 h. The reaction was quenched by addition of ice-cold water (5 mL) and then submitted to standard workup with CH$_2$Cl$_2$. The crude product was purified by FC (EtOAc/Hexanes, 35/65 to 45/55, V/V) to provide a light yellow solid 12 (0.158 g, 61%). $^1$H NMR (200 MHz, CDCl$_3$) δ 6.70 (br s, 1H), 6.11 (s, 2H), 5.34-5.17 (m, 1H), 5.14-5.00 (m, 0.5H), 4.89-4.75 (m, 0.5H), 4.63-4.32 (m, 3H), 3.80 (s, 9H), 2.63-2.05 (m, 2H), 1.44 (s, 9H), 1.42 (s, 9H). $^{13}$C NMR (50 MHz, CDCl$_3$) δ 171.0, 170.9, 168.8, 168.4, 161.3, 159.5, 155.6, 155.3, 106.2, 106.1, 91.1, 91.0, 90.8, 87.4, 87.3, 82.41, 82.36, 80.0, 77.4, 55.9, 55.5, 51.1, 36.1, 35.6, 35.2, 32.2, 28.4, 28.1.

HRMS calcd for C$_{24}$H$_{38}$FN$_2$O$_8$ (M+H)$^+$: 501.2612. found: 501.2591.

Ref: RajanBabu, T. V.; Middleton, W. J.; Tortorelli, V. J., Tris(dimethylamino)sulfonium Difluorotrimethylsilicate. *e-EROS Encyclopedia of Reagents for Organic Synthesis* 2001.

Procedure for fluorination by "neutralized" TASF: synthesis of (2S,4R)-tert-butyl 2-(tert-butoxycarbonylamino)-4-fluoro5-oxo-5-(2,4,6-trimethoxybenzyl amino)pentanoate (12')

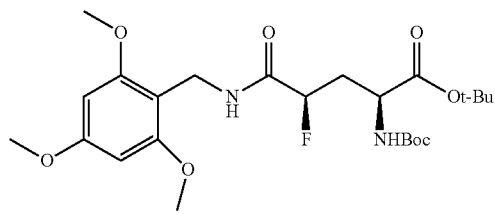 [SMILES: COc1cc(OC)c(CNC(=O)[C@H](F)C[C@H](NC(=O)OC(C)(C)C)C(=O)OC(C)(C)C)c(OC)c1]

To a stirred solution of tris(dimethylamino)sulfonium difluorotrimethylsilicate (TASF, 1.38 g, 5.0 mmol) in CH$_2$Cl$_2$/THF (1.5 mL/1.5 mL) was added Et$_3$N(HF)$_3$ (0.25 mL) dropwise. After that, tosylate 11' (0.391 g, 0.6 mmol), THF (1 mL) and above "neutralized" TASF (2.7 mL, 3.0 mmol) were added one by one to a 25 mL two-neck flask equipped with a reflux condenser. The mixture was heated to 50° C. by oil bath for 10 h, the oil bath was removed, the reaction mixture was diluted with EtOAc and washed with half saturated NaHCO$_3$, water and brine subsequently. The EtOAc phase was collected, dried by MgSO$_4$, filtered, concentrated in vacuo. The left residue was purified by FC (EtOAc/Hexanes, 25/75 to 40/60, V/V) to provide a pale white foamy solid 12' (0.232 g, $^{77}$%); [α]$^{24}_D$+1.70 (c=1.14, MeOH); HPLC of 12': [99%, major peak: Rt=22.8 min; 1%, minor peak: Rt=25.2 min; column: Chiralcel OD (250×4.6 mm), UV detector, 210 nm, 1.5% EtOH in hexanes; flow rate: 1.2 mL/min]. $^1$H NMR (200 MHz, CDCl$_3$) δ 6.69 (br s, 1H), 6.12 (s, 2H), 5.32 (d, 1H, J=8.6 Hz), 5.13 (dd, 0.5H, J$_1$=8.8 Hz, J$_2$=3.2 Hz), 4.88 (dd, 0.5H, J$_1$=8.8 Hz, J$_2$=3.2 Hz), 4.60 (dd, 1H, J$_1$=13.6 Hz, J$_2$=6.0 Hz), 4.42-4.34 (m, 2H), 3.81 (s, 9H), 2.64-2.06 (m, 2H), 1.45 (s, 9H), 1.43 (s, 9H). $^{13}$C NMR (50 MHz, CDCl$_3$) δ 170.9, 168.8, 168.4, 161.3, 159.5, 155.3, 106.2, 91.2, 90.8, 87.5, 82.5, 80.0, 56.0, 55.6, 51.2, 35.7, 35.3, 32.2, 28.5, 28.1. HRMS calcd for C$_{24}$H$_{38}$FN$_2$O$_8$ (M+H)$^+$: 501.2612. found: 501.2613.

Crystals of 12' suitable for X-ray crystal structure analysis were obtained from a slow solvent evaporation of CH$_2$Cl$_2$/Hexanes solution of 12'.

Crystal Structure of Intermediate 12':

After that, tosylate 11" (0.434 g, 0.66 mmol), THF (1 mL) and above "neutralized" TASF (4.4 mL, 5.2 mmol) were added one by one to a 25 mL two-neck flask equipped with a reflux condenser. The mixture was heated to 45° C. by oil bath for 24 h, the oil bath was removed, the reaction mixture was diluted with EtOAc and washed with half saturated NaHCO$_3$, water and brine subsequently. The EtOAc phase was collected, dried by MgSO$_4$, filtered, concentrated in vacuo. The left residue was purified by FC (EtOAc/Hexanes, 25/75 to 40/60, V/V) to provide a pale white foamy solid 12" (0.101 g, 30%); [α]$^{22}_D$=−18.4 (c=1.10, MeOH); HPLC of 12": [96.6%, major peak: Rt=20.5 min; 3.4%, minor peak: Rt=19.0 min; column: Chiralcel OD (250×4.6 mm), UV detector, 210 nm, 1.5% EtOH in hexanes; flow rate: 1.2 mL/min]. $^1$H NMR (200 MHz, CDCl$_3$) δ 6.73 (d, 1H, J=3.8 Hz), 6.14 (s, 2H), 5.15 (d, 1H, J=8.8 Hz), 5.06 (dd, 0.5H, J$_1$=9.2 Hz, J$_2$=3.0 Hz), 4.81 (t, 0.5H, J=6.4 Hz), 4.61-4.35 (m, 3H), 3.83 (s, 9H), 2.41-2.18 (m, 2H), 1.46 (s, 9H), 1.44 (s, 9H). $^{13}$C NMR (50 MHz, CDCl$_3$) δ 171.1, 168.8, 168.4, 161.3, 159.5, 155.7, 106.0, 91.0, 90.7, 87.3, 82.4, 80.0, 56.0, 55.5, 51.02, 36.2, 35.8, 32.2, 28.4, 28.1. HRMS calcd for C$_{24}$H$_{38}$FN$_2$O$_8$ (M+H)$^+$: 501.2612. found: 501.2615.

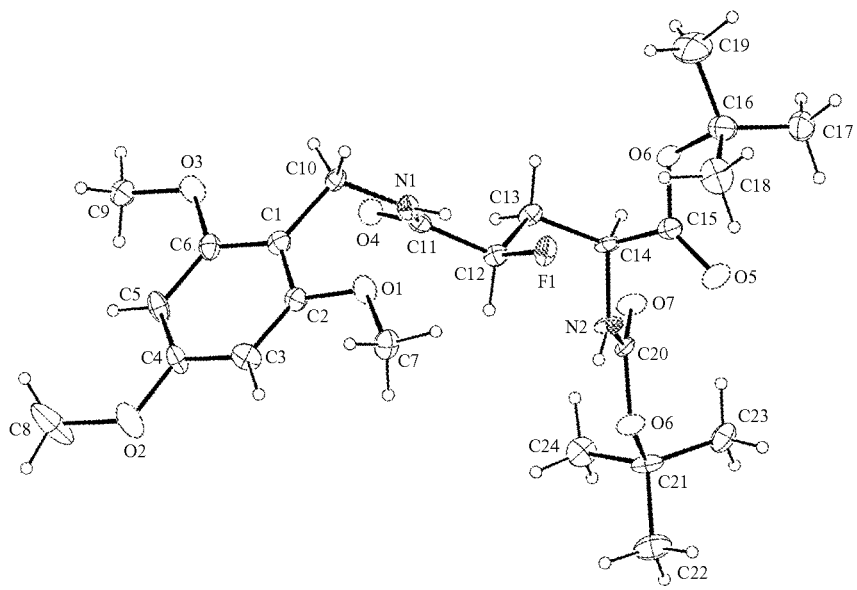

(2S,4S)-tert-butyl-2-(tert-butoxycarbonylamino)-4-fluoro5-oxo-5-(2,4,6-trimethoxy benzylamino)pentanoate (12")

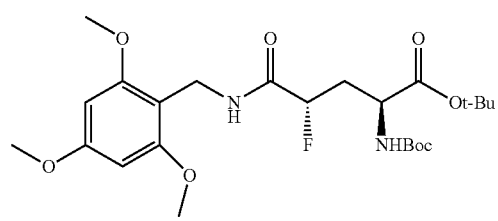 [SMILES: COc1cc(OC)c(CNC(=O)[C@@H](F)C[C@H](NC(=O)OC(C)(C)C)C(=O)OC(C)(C)C)c(OC)c1]

To a stirred solution of tris(dimethylamino)sulfonium difluorotrimethylsilicate (TASF, 1.43 g, 5.2 mmol) in CH$_2$Cl$_2$/THF (1.5 mL/1.5 mL) was added Et$_3$N(HF)$_3$ (0.26 mL) dropwise.

(2S,4R)-2,5-Diamino-4-fluoro-5-oxopentanoic acid (1)

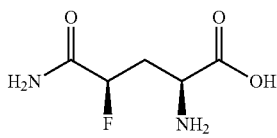

To a mixture of 12' (0.192 g, 0.384 mmol) with dimethylsulfide (0.1 mL) cooled with an ice bath (0° C.), trifluoroacetic acid (TFA, 5 mL) was added dropwise. After addition, the ice bath was removed and the reaction was kept at r.t. for 2.5 h. The solution was evaporated in vacuo to remove most TFA. The residue was dissolved in H$_2$O (5 mL) and washed with CH$_2$Cl$_2$ (3 mL×2). The aqueous part was cooled in an ice bath and neutralized to pH=7 by slow addition of ice-cold 5% aqueous ammonia. The neutralized solution was submitted to a small column of Dowex 50WX8-200 (H+ form, 10 g), washed with water and further eluted with 5% aqueous ammonia. The fractions containing product were pooled and concentrated in vacuo and dried in the high vacuum condition overnight to afford crude product as a white solid. It was further purified by re-crystallization from EtOH/H$_2$O to provide a white solid (0.045 g, 71% yield): mp 175° C. (dec); $[\alpha]^{25}_D$=+46.2 (c=0.16, H$_2$O); HPLC of 1: [98.8%, major peak: Rt=11.98 min; 1.22%, minor peak: Rt=9.29 min; column: Chirex 3126 (D)-penicillamine (150×4.6 mm), UV detector, 254 nm, 1.0 mM CuSO$_4$ solution; flow rate: 1.0 mL/min, column temperature 10° C.];

$^1$H NMR (200 MHz, D$_2$O) δ 5.41 (dd, 0.5H, J$_1$=10.0 Hz, J$_2$=3.0 Hz), 5.17 (dd, 0.5H, J$_1$=10.0 Hz, J$_2$=3.0 Hz), 3.97 (t, 1H, J=6.6 Hz), 2.74-2.24 (m, 2H); $^{13}$C NMR (50 MHz, D$_2$O+ trace CD$_3$OD) δ 175.1, 174.7, 174.2, 91.8, 88.2, 53.2, 34.7, 34.3; $^{19}$F NMR (282 MHz, D$_2$O+trace CD$_3$OD) δ −188.2 (H—F decoupled); HRMS calcd for C$_5$H$_{10}$FN$_2$O$_3$ (M+H)$^+$: 165.0675. found: 165.0683.

Crystals of 4-FGln 1 suitable for X-ray crystal structure analysis were obtained from a slow solvent evaporation of H$_2$O solution of 1. Crystal structure of final 4-FGln (2S,4R), 1:

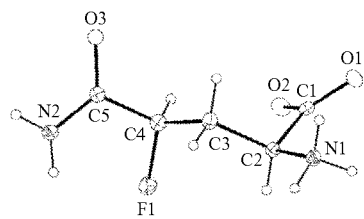

Ref: Vladimir Tolman, Petr Sedmera. *Journal of Fluorine Chemistry* 2000, 101, 5-10

(2S,4S)-2,5-Diamino-4-fluoro-5-oxopentanoic acid (2)

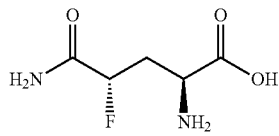

Following the procedure in the preparation of 1, compound 2 was prepared from fluoride 12" (0.090 g, 0.18 mmol) as a white solid (0.019 g, 67% yield): mp 160° C. (dec); $[\alpha]^{25}_D$=−14.6 (c=0.15, H$_2$O); HPLC of 2: [94.9%, major peak: Rt=10.8 min; 5.1%, minor peak 1: Rt=8.42 min; column: Chirex 3126 (D)-penicillamine (150×4.6 mm), UV detector, 254 nm, 1.0 mM CuSO$_4$ solution; flow rate: 1.0 mL/min, column temperature 10° C.]; $^1$H NMR (200 MHz, D$_2$O) δ 5.36 (t, 0.5H, J=6.2 Hz), 5.12 (dd, 0.5H, J$_1$=7.8 Hz, J$_2$=4.6 Hz), 4.02 (t, 1H, J=5.8 Hz), 2.63 (t, 1H, J=6.0 Hz), 2.49 (pentet, 1H, J=3.8 Hz); $^{13}$C NMR (50 MHz, D$_2$O+trace CD$_3$OD) δ 174.9, 174.5, 174.0, 91.4, 88.2, 87.8, 52.8, 34.3, 33.9; $^{19}$F NMR (282 MHz, D$_2$O+ trace CD$_3$OD) δ −188.13 (H—F decoupled); HRMS calcd for C$_5$H$_{10}$FN$_2$O$_3$ (M+H)$^+$: 165.0675. found: 165.0664.

Radiofluorination Methods.

To avoid racemization during the $^{18}$F labeling reaction, a combination of a mild basic agent potassium bicarbonate (KHCO$_3$) and a neutral phase transfer catalyst, 18-Crown-6, was tested for the "hot" fluorination reaction. Using the tosylate precursor, the desired (2S,4R) isomer [$^{18}$F]12' was successfully formed as the major product accompanied by a small portion of carbon-2 position epimerized (2R,4R) diastereomer [$^{18}$F]12a". Subsequently, desired de-protected product, [$^{18}$F]1, was finally prepared by treating intermediate [$^{18}$F]12' with TFA/anisole at 60° C. for 5 min. Direct identification of [$^{18}$F]1 by co-eluting on HPLC was problematic, since 4-FGln does not show substantial UVN is absorbance. The product was treated with (9-fluorenylmethyl) carbamate chloride (Fmoc-Cl) to perform the amino-Fmoc protection. This further derivatized radioactive compound, Fmoc-[$^{18}$F]1, was identified on the HPLC profile by co-injecting with the "cold" Fmoc-4-FGln standard. Ultimately, by using a chiral column Phenomenex® Chiral Chirex3126 (D-penicillamine) (150×4.6 mm) with aqueous 1 mM CuSO$_4$ solution as eluent (1 mL/min, 10° C. column temperature) we could separate and identify all four radio labeled and cold 4F-Gln 1, 2, 3 and 4 without the need of further derivatization (Cu-4-FGln complexes are UV absorbing) [$^{18}$F]1 was indeed the major product accompanied by a small amount of diastereomer [$^{18}$F]4 (<5%).

HPLC profiles of all four radio labeled 4F-Gln and the "cold" standards can be ascertained using Chiral Chirex3126 (D-penicillamine) (150×4.6 mm) 1 mM CuSO$_4$, 1 mL/min, 10° C. Using these conditions, compound 2 elutes first, followed by compound 1, 3, and 4. See FIG. 5.

Radiosynthesis of [$^{18}$F]1 ((2S,4R)-4-FGln) with 11' as Starting Material

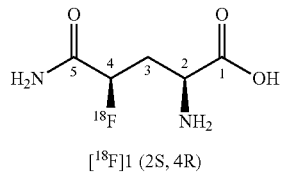

[$^{18}$F]1 (2S, 4R)

An activated SepPak® Light QMA Carb was loaded with F18 (20 to 40 mCi) and eluted with 1 mL 18-c-6/KHCO$_3$ (160 mg 18-c-6 in 18.6 mL ACN/29 mg KHCO$_3$ in 3.4 mL water). the solution was blown to dryness with argon and twice azeotropically dried with 1 mL acetonitrile at 80° C. under a flow of argon. The dried F18 was cooled in an ice bath and 5 mg of 11' was dissolved in 0.5 ml acetonitrile and added to the dried F18. The mixture was heated for 15 minutes at 70° C. oil bath. The mixture was cooled in icebath, 0.5 mL acetonitrile and 8 mL water were added. The mixture was loaded onto an activated Oasis® HLB 3cc, pushed through and washed twice with 3 mL water. The desired radiolabeled compound was eluted with 0.5 mL ethanol (~20% of the total radioactivity). Radiochemical purity was determined by reversed phase HPLC (Gemini C18 (250×4.6 mm), MeOH/0.1% formic acid 8/2. 1 mL/min, ret. time ~6 min, >95%), stereochemical purity was determined by chiral HPLC (Chiralpak OD column (250×4.6 mm), hexanes/EtOH 98.5/1.5, 1.2 mL/min, ret. time ~22 minutes >95%).

Figure 6:
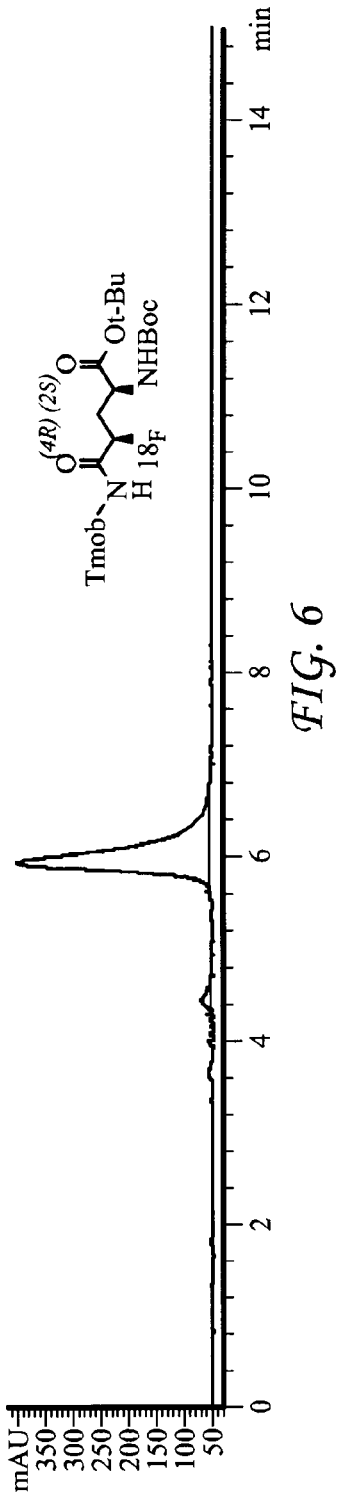
FIG. 6 depicts HPLC profile of intermediate 12' on reversed phase HPLC (Gemini C18 (250×4.6 mm), MeOH/0.1% formic acid 8/2. 1 mL/min, ret.time ~6 min, >95%.
Figure 7:
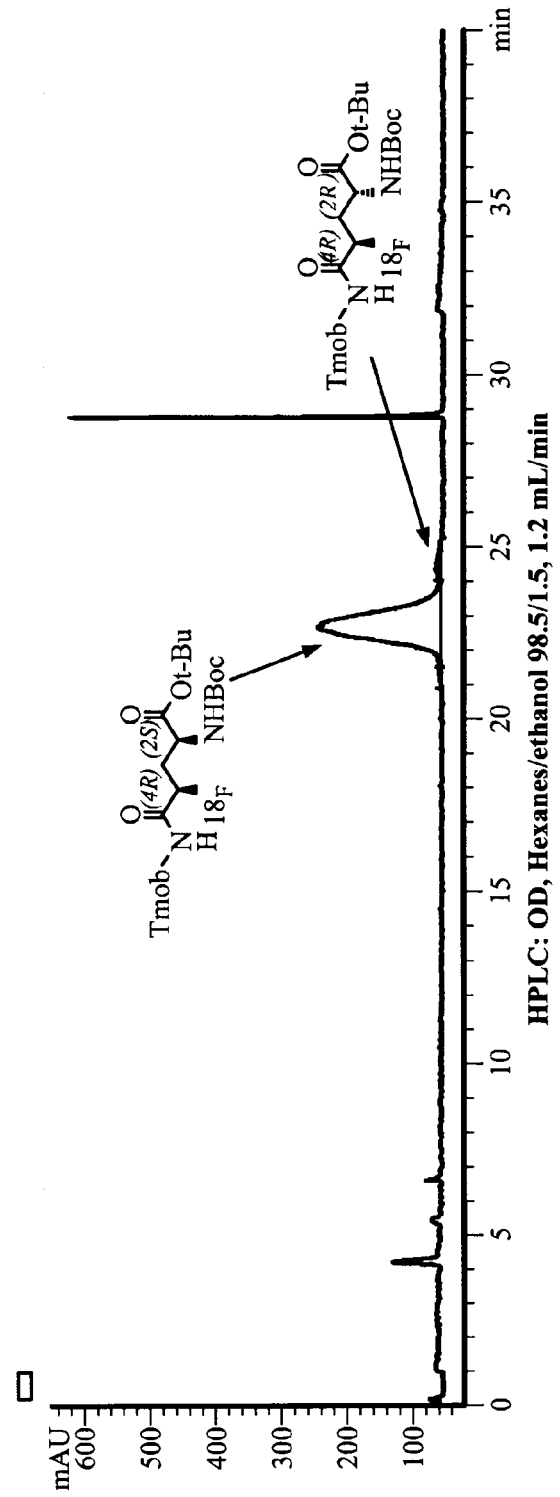
FIG. 7 depicts an HPLC profile of intermediate 12' on Chiralpak OD column (250×4.6 mm), hexanes/EtOH 98.5/1.5, 1.2 mL/min, ret.time ~22 minutes, dr ~96%).
Figure 8:
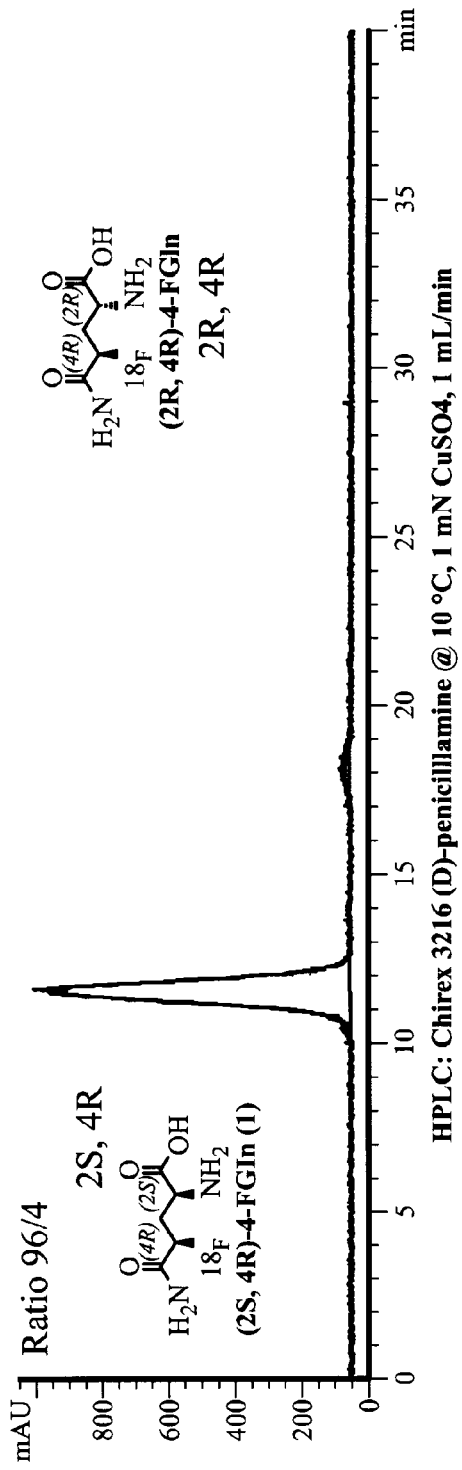
FIG. 8 depicts an HPLC profile of [18F]1 ((2S,4R)-4-FGln) on chiral column (Chirex 3126 (d)-penicillamine, 1 mM CuSO4 solution, 1 mL/min, ret. time for the 2S,4R isomer ~11 minutes, the 2R,4R isomer ~18 minutes).

The ethanolic solution was blown to dryness, cooled in an ice bath and a mixture of 595 μL TFA/5 μL anisole was added. The solution was heated for 5 minutes at 60° C. TFA and anisole were removed while still warm under a stream of argon; the residue was titurated with 1 mL water; the aqueous solution was filtered through a 0.45 µ filter to yield the desired radio active [$^{18}$F]1 ((2S,4R)-4-FGln) in about 10% isolated yield, non decay corrected; RCP 99%; dr: 96%. The radiochemical purity and stereochemical purity was determined by chiral HPLC (Chirex 3126 (d)-penicillamine, 1 mM CuSO4 solution, 1 mL/min, ret. time for the 2S,4R isomer ~11 minutes, the 2R,4R isomer ~18 minutes). See FIGS. 6, 7, and 8.

Radiosynthesis of [$^{18}$F]3 ((2R,4S)-4-FGln) with 11a' as Starting Material

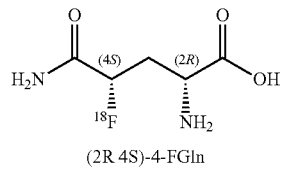

(2R 4S)-4-FGln

An activated SepPak® Light QMA Carb was loaded with F18 (39.8 mCi) and eluted with 1 mL 18-c-6/KHCO$_3$ (160 mg 18-c-6 in 18.6 mL ACN/29 mg KHCO$_3$ in 3.4 mL water). the solution was blown to dryness with argon and twice azeotropically dried with 1 mL acetonitrile at 80° C. under a flow of argon. The dried F18 was cooled in an ice bath and 5 mg of was dissolved in 0.5 ml acetonitrile and added to the dried F18. The mixture was heated for 15 minutes at 70° C. oil bath. The mixture was cooled in icebath, 0.5 mL acetonitrile and 8 mL water were added. The mixture was loaded onto an activated Oasis® HLB 3cc, pushed through and washed twice with 3 mL water. The desired radiolabeled compound was eluted with 0.5 mL ethanol (~20% of the total radioactivity). Radiochemical purity was determined by reversed phase HPLC (Gemini C18 (250×4.6 mm), MeOH/0.1% formic acid 8/2. 1 mL/min, ret.time ~6 min, RCP >95%), stereochemical purity was determined by chiral HPLC (Chiralpak OD column (250×4.6 mm), hexanes/EtOH 98.5/1.5, 1.2 mL/min, ret.time ~20 minutes dr >90%).

Figure 9:
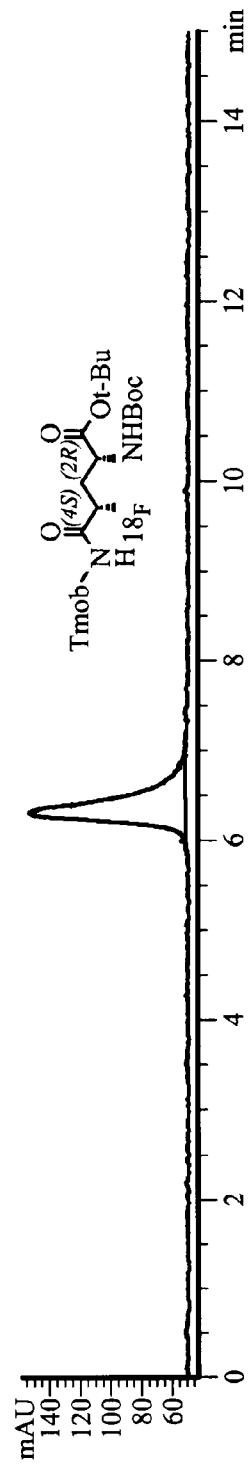
FIG. 9 depicts an HPLC profile of intermediate 12a' on reversed phase HPLC (Gemini C18 (250×4.6 mm), MeOH/0.1% formic acid 8/2. 1 mL/min, ret.time ~6 min, >95%.
Figure 10:
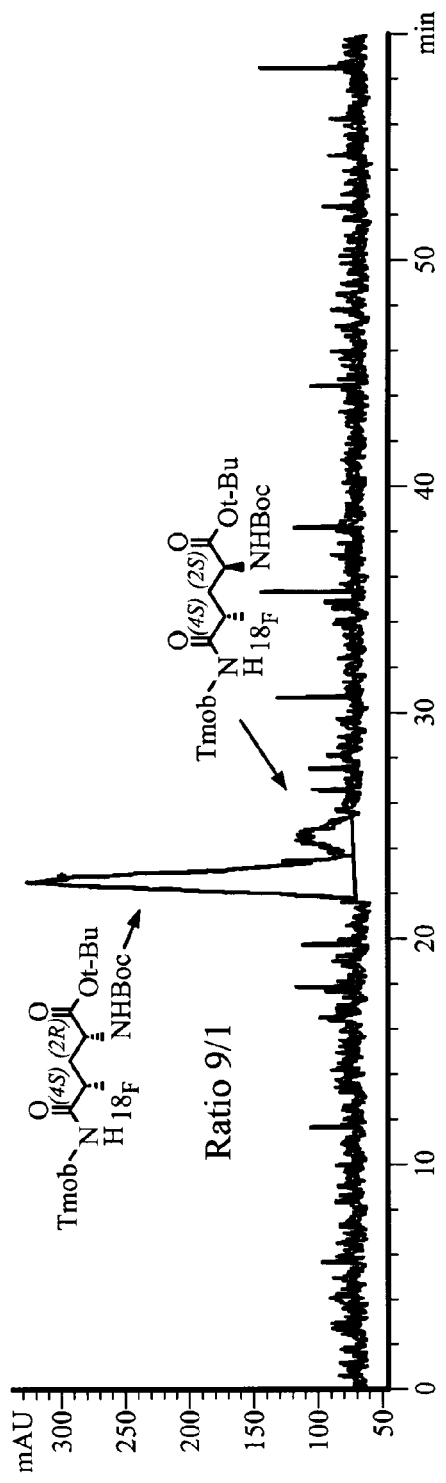
FIG. 10 depicts an HPLC profile of intermediate 12a' on Chiralpak OD column (250×4.6 mm), hexanes/EtOH 98.5/1.5, 1.2 mL/min, ret.time ~22 minutes, dr ~96%).
Figure 11:
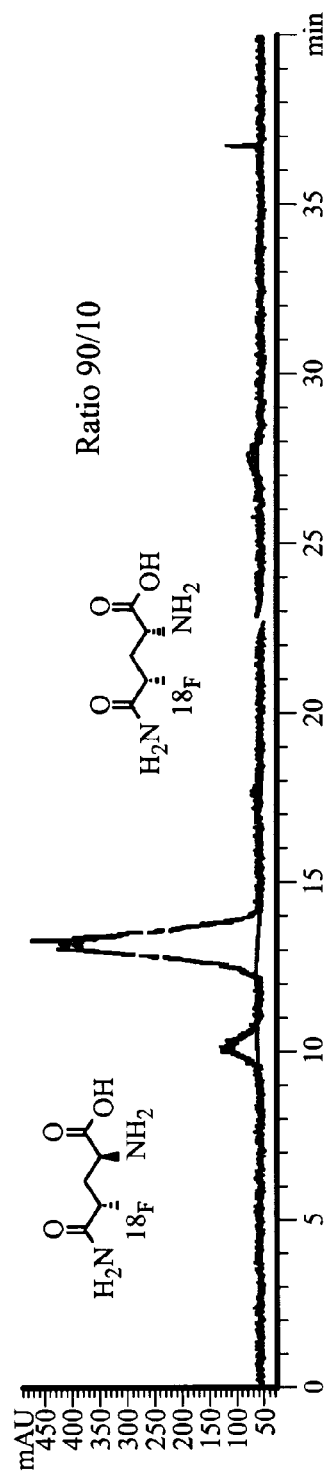
FIG. 11 depicts an HPLC profile of [18F]3 ((2R,4S)-4-FGln) on chiral column (Chirex 3126 (d)-penicillamine, 1 mM CuSO4 solution, 1 mL/min, ret. time for the 2R,4S isomer ~15 minutes, the 2S,4S isomer ~10 minutes).

The ethanolic solution was blown to dryness, cooled in an ice bath and a mixture of 595 µL TFA/5 µL anisole was added. The solution was heated for 5 minutes at 60° C. TFA and anisole were removed while still warm under a stream of argon; the residue was titurated with 1 mL water; the aqueous solution was filtered through a 0.45 µl filter to yield the desired radio active [$^{18}$F]3 ((2R,4S)-4-FGln) in about 10% isolated yield, non decay corrected; RCP 97%; dr: 90%. The radiochemical purity and stereochemical purity was determined by chiral HPLC (Chirex 3126 (d)-penicillamine, 1 mM CuSO4 solution, 1 mL/min, ret. time for the 2R,4S isomer ~15 minutes, the 2S,4S isomer ~10 minutes). See FIGS. 9, 10, and 11.

Radiosynthesis of [$^{18}$F]2((2S,4S)-4-FGln)

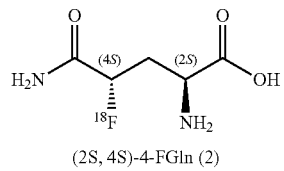

(2S, 4S)-4-FGln (2)

An activated SepPak® QMA was loaded with F18 (46.9 mCi) and eluted with 1 mL K222/K$_2$CO$_3$ (220 mg K222 in 18.6 mL acetonitrile/40 mg K$_2$CO$_3$ in 3.4 mL water) (45.5 mCi). The solution was blown to dryness with argon and twice azeotropically dried with 1 mL acetonitrile at 80° C. under a flow of argon. The dried F18 was cooled in an ice bath and 5.31 mg of 11" was dissolved in 1 ml acetonitrile and added to the dried F18. The mixture was heated for 20 minutes at 70° C. oil bath. The mixture was cooled in icebath and 8 mL water were added. The mixture was loaded onto an activated Oasis® HLB 3cc, pushed through and washed twice with 3 mL water. The desired radiolabeled compound was eluted with 0.5 mL ethanol (~14% of the total radioactivity).

Figure 12:
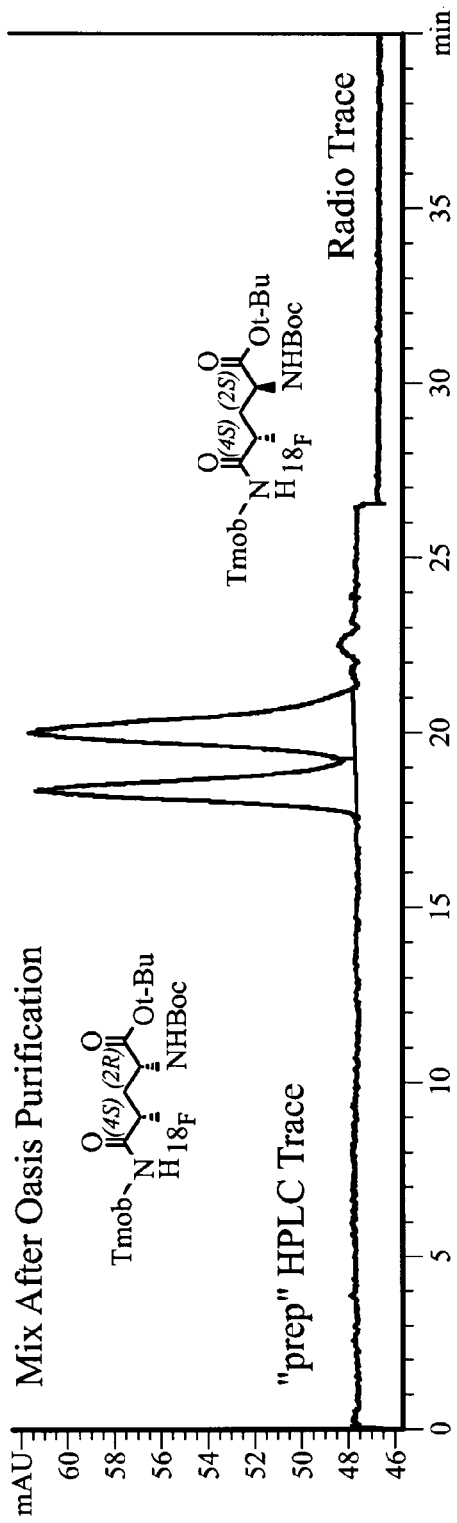
FIG. 12 depicts a radioactive HPLC trace of ethanolic solution (mix of [18F]12" and [18F]12a') on Chiral OD column, hexanes/EtOH 98.5/1.5, flowrate 1.2 ml/min.

The ethanolic solution was concentrated to about 200 µL volume and 5 µL were injected into chiral HPLC (OD-column, hexanes/EtOH 98.5/1.5 1.2 mL/min) and the second peak (~20 minutes) was isolated. Second peak which corresponds to the 2S,4S isomer was isolated (56 µCi) (fractions collected were around ret time of 20 min were: 45/4/56 µCi respectively). See FIG. 12.

Hexanes/ethanol solution of desired fraction was blown to dryness, 219 µL TFA/1 µL anisole was added and heated for 5 minutes at 60° C. Volatiles were removed under argon while still warm. Residue was treated with 0.5 mL water and transferred into new vial to give dose: 46 µCi (RCP >99%, E>98%).

Figure 13A:
FIGS. 13A, 13B, and 13C depict HPLC traces of purified [18F]2 ((2S,4S)-4-FGln on chiral column (Chirex 3126 (d)-penicillamine, 1 mM CuSO4 solution, 1 mL/min, Identity was established by coinjection with the cold standard.
Figure 13B:
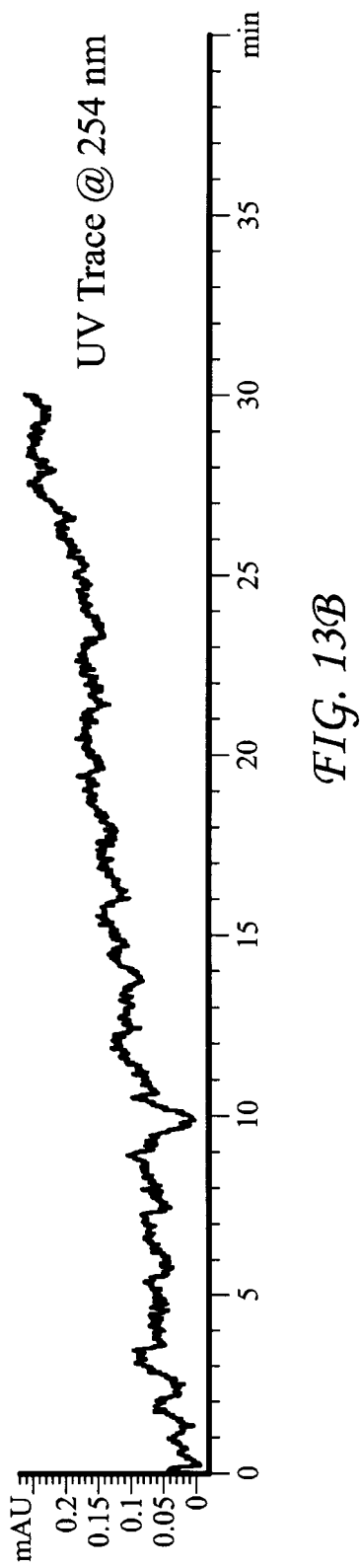
Figure 13C:
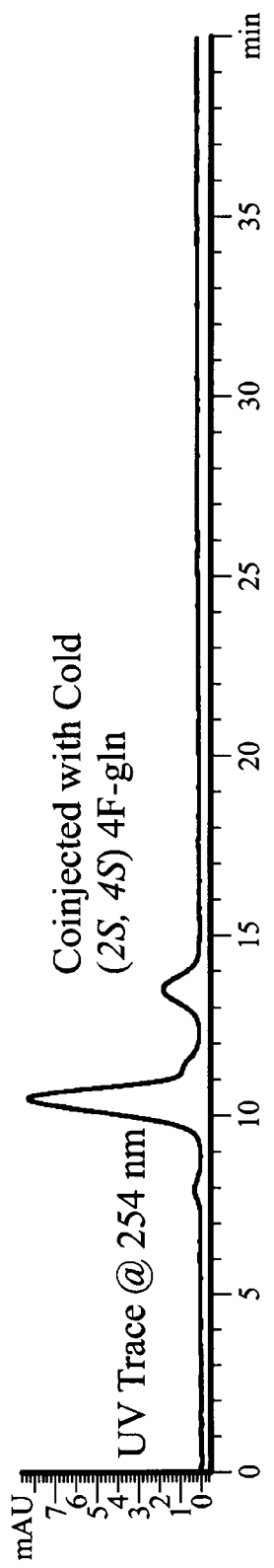

Radiochemical purity, identity and diastereomeric purity was determined by HPLC: See FIG. 13.

Radiosynthesis of [$^{18}$F]4 ((2R,4R)-4-FGln)

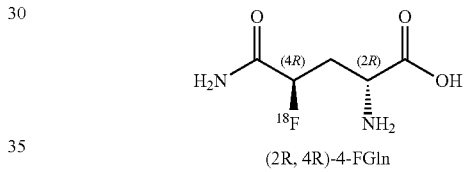

(2R, 4R)-4-FGln

An activated SepPak® QMA was loaded with F18 (82.8 mCi) and eluted with 1 mL K222/K$_2$CO$_3$ (220 mg K222 in 18.6 mL acetonitrile/40 mg K$_2$CO$_3$ in 3.4 mL water) (78.9 mCi). The solution was blown to dryness with argon and twice azeotropically dried with 1 mL acetonitrile at 80° C. under a flow of argon. The dried F18 was cooled in an ice bath and 8.28 mg of 11a" was dissolved in 1 ml acetonitrile and added to the dried F18. The mixture was heated for 20 minutes at 70° C. oil bath. The mixture was cooled in icebath and 8 mL water were added. The mixture was loaded onto an activated Oasis® HLB 3cc, pushed through and washed twice with 3 mL water. The desired radiolabeled compound was eluted with 0.5 mL ethanol (~14% of the total radioactivity).

The ethanolic solution was concentrated to about 200 µL volume and 5 µl were injected into chiral HPLC (OD-column, hexanes/EtOH 98.5/1.5 1.2 mL/min) and the second peak (~24 minutes) was isolated. Second peak which corresponds to the 2R,4R isomer was isolated (106 µCi). See FIG. 14.

Hexanes/ethanol solution of desired fraction was blown to dryness, 219 µL TFA/1 µL anisole was added and heated for 5 minutes at 60° C. Volatiles were removed under argon while still warm. Residue was treated with 0.5 mL water and transferred into new vial to give dose: 103 µCi (RCP >99%, dr >99%).

Figure 15B:
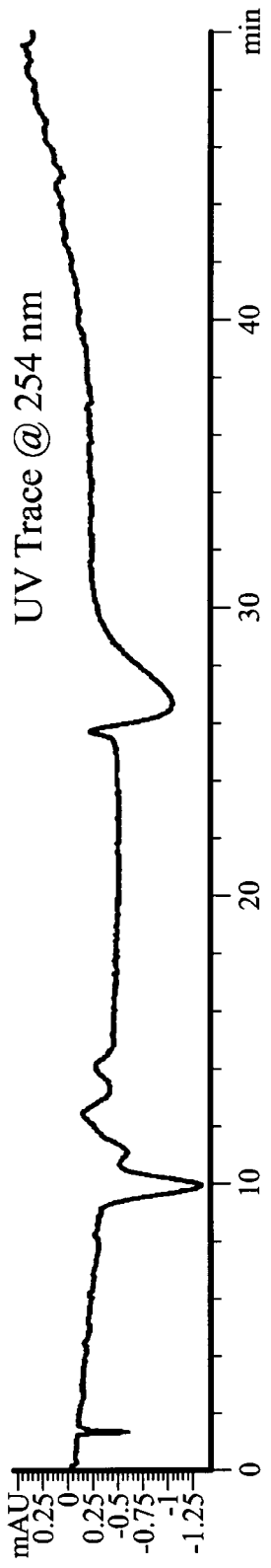
Figure 15C:
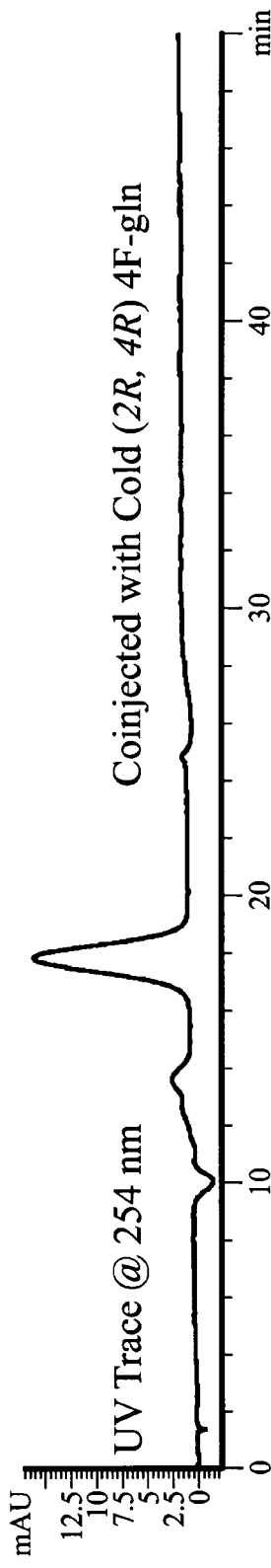

Radiochemical purity, identity and enantiomeric purity was determined by HPLC. See FIG. 15.

Biological Study Procedures:
In Vitro Cell Uptake Studies

Figure 4:
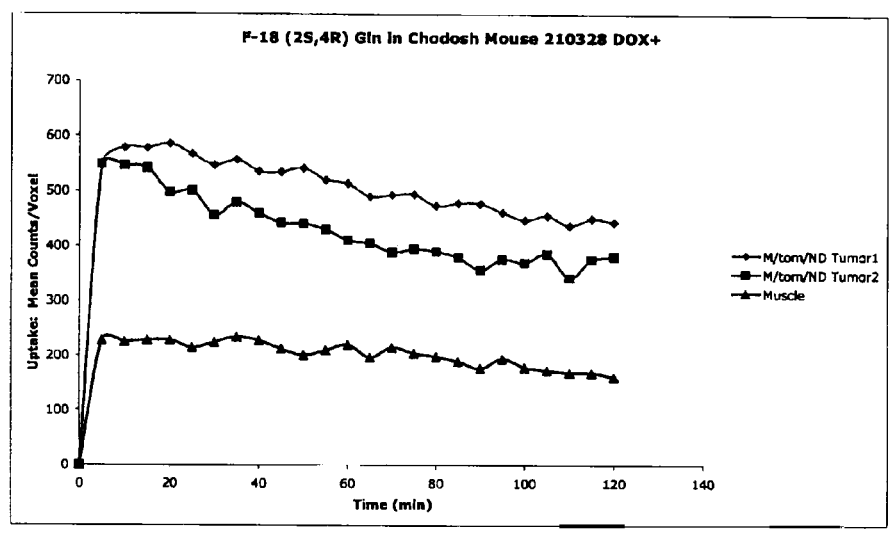
FIG. 4 depicts the uptake of compound 1 in a mouse.

Cell uptake of four possible isomers was evaluated using 9 L tumor cell line. The cell uptake results (% dose/100 µg protein) were compared to that of [³H] glutamine. The uptake of 4-fluoro-glutamine isomers showed distinctive differences between the isomers (FIG. 4). The 2S isomers, the natural L-glutamine derivatives, displayed the highest uptake. The 4-FGln (2S,4R) showed a high uptake in 9 L cells and the uptake continued non-stop for 2 hours, the maximum time point studied. The 4-FGln (2S,4R) isomer also displayed excellent uptake similar to that of (2S,4R) isomer; however, it appeared that the uptake value dropped precipitously at 2 hours. The un-natural D-glutamine isomers, (2R,4R) and (2R,4S) 4-FGln, all showed a lower cell uptake as compared to the (2S,4R) and (2S,4S) 4-FGln as well as the [³H]-L-glutamine, suggesting that the configuration at the C-2 position is very critical for tumor cell uptake, and the 2S configuration of glutamine (commonly known as the L-isomer) is essential for transportation across cell membrane. See FIG. 1

The tumor cell uptake of [$^{18}$F]4-FGln is a highly selective process, the two native 4-fluoro-L-glutamine derivatives displayed a higher uptake than those of the un-natural 4-fluoro-D-glutamine derivatives.

Figure 2:
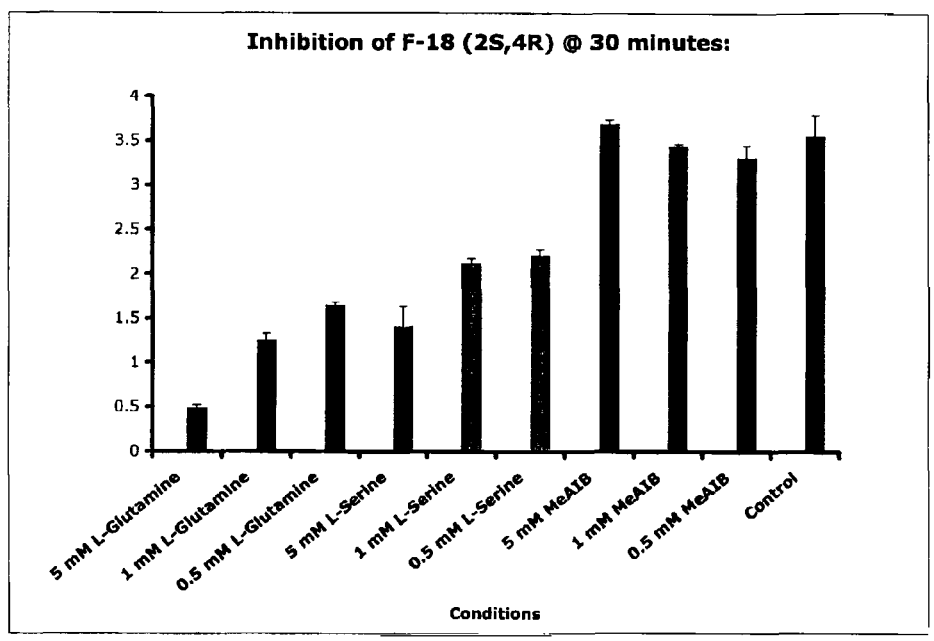
FIG. 2 depicts the % uptake/100 ug protein of 1. The x axis is % uptake/100 ug protein

The [$^{18}$F]4-FGln (2S,4R), 1 isomer displayed the highest uptake into 9 L tumor cells amongst the other [$^{18}$F]4-FGln isomers. Because of this observation, we decided only to further investigate the (2S,4R) isomer of [$^{18}$F]4-FGln, 1. In vitro cell uptake inhibition studies were conducted in 9 L cells in order to test the specificity of [$^{18}$F]4-FGln (2S,4R), 1. Cold L-glutamine and L-serine served as the positive control inhibitors for the glutamine transporters. L-glutamine inhibits system N transporter and L-serine inhibits the ASC transporter. Three different concentrations were tested for each inhibitor ranging from 0.5 mM to 5 mM. After 30 minutes of co-incubation of L-glutamine and [$^{18}$F] (2S,4R)-4-FGln, 1, the system N transporter was clearly inhibited. Results showed nearly 90% inhibition (0.49% dose/100 ug protein inhibited vs. control 3.56% dose/100 ug protein). L-serine also showed considerable inhibition (1.41% inhibited vs control 3.56% dose/100 ug protein) of the ASC transporter. Cold MeAIB served as the negative control, which inhibits system A transporter. At a concentration of 5 mM, there was little to no effect on the system A transport system (3.69% inhibited vs. control 3.56% dose/100 ug protein). The results clearly demonstrate a dose dependent response to L-glutamine and L-serine, with MeAIB showing no inhibition on system A transport system. See FIG. 2

The cellular uptake of each of the four 4-[$^{18}$F]F-glutamine isomers (2S,4R), (2S,4S), (2R,4S) and (2R,4R) were studied in (9 L) rat brain gliosarcoma cells. L-[3,4-³H(N)]-glutamine, >97%, 250 µCi (9.25 MBq), was purchased from Perkin Elmer and was used as a control for all of the cellular uptake experiments conducted. The purity of L-[3,4-³H(N)]-glutamine was determined by a TLC method (TLC Silica gel 60 F$_{254}$; Solvent CH$_2$Cl$_2$: MeOH: NH$_3$:H$_2$O (20:20:5). The L-[3,4-³H(N)]-glutamine showed an Rf value between 0.3-0.4. Rodent (9 L) cells were cultured in Dulbecco's modified Eagle's medium (DMEM), fetal bovine serum and 100 units/mL Penicillin, 100 µg/mL Streptomycin. Tumor cells were plated (2.0×10⁵ cells/well) 24 h in the media prior to ligand incubation. On the day of experiment, the media was aspirated and the cells were washed 3 times with 1 mL with warm phosphate buffered saline (PBS, containing 0.90 mM of Ca$^{2+}$ and 1.05 mM of Mg$^{2+}$). All four of the 4-[$^{18}$F]F-glutamine isomers and the L-[3,4-³H(N)]-glutamine was dissolved in PBS solution and was added to each well (500,000 cpm/mL/well) and incubated at 37° C. for 5, 30, 60, 120 min. At the end of the incubation period, the wells were aspirated and then the residual cells were washed 3 times with 1 mL ice cold PBS without Ca$^{2+}$ and Mg$^{2+}$. After washing with cold PBS, 350 µL 1M NaOH was used to lyse the cells. The lysed cells were collected onto filter paper. The filter papers were placed in scintillation vials and counting fluid was added (7 mL ecolite+) and the vials were then counted with a beta counter 18-24 h later. For dual-isotope studies using 4-[$^{18}$F]F-glutamine isomers and L-[3,4-³H(N)]-glutamine, the vials were counted first using a gamma counter to obtain $^{18}$F counts. The beta counts were then obtained one day later after the $^{18}$F was fully decayed. 100 µL of the cell lysate was used for the determination of the protein concentration by Lowry method.

In Vitro Inhibition Studies:

To test the specificity of the 4-[$^{18}$F]F-glutamine (2S,4R) isomer, inhibition studies were conducted using 9 L cells. The tracer was incubated at 37° C. for 30 min. The cells were processed as previously described as above. Cold L-glutamine and L-Serine served as the positive control inhibitors for the glutamine transporters. L-glutamine inhibits system N transporter and L-Serine inhibits the ASC transporter. Cold MeAIB served as the negative control, which inhibits system A transporter. Three different concentrations were tested for each inhibitor ranging from 0.5 mM to 5 mM. Data showed a dose dependent response to each inhibitor with L-glutamine showing most inhibition (~90% at [5 mM]).

Small Animal Imaging with a microPET

Dynamic small animal PET (A-PET) imaging studies were conducted with 4-[$^{18}$F]F-glutamine (2S,4R) isomer. All scans were performed on a dedicated animal PET scanner (Mosaic by Phillips) (Surti, 2005). Transgenic mice bearing M/tomND spontaneous human mammary tumors were used in this study. There are many advantages to using this transgenic mouse model. A doxycycline sensitive promoter genetically engineers these mice to express the myc gene. These tumors spontaneously arise vs. traditional xenograph tumors. When the mice are administered doxycycline through their drinking water (2 mg/kg) the expression of the myc gene is up-regulated. When doxycycline is removed, the myc gene is down regulated. This model was chosen because these compounds will allow a direct correlation between true glutamine uptake and the level of myc gene expression.

Figure 3:
FIG. 3 depicts a dynamic small animal PET image of a mouse injected with compound 1

Glutamine uptake within the M/tomND tumor was examined by injecting ~300 µCi of the [$^{18}$F]-4F-glutamine (2S,4R) isomer via the lateral tail vein. Imaging commenced immediately after the injection of the tracer and continued for a time period of 120 minutes. The images and kinetic of tumor uptake clearly demonstrated that the [$^{18}$F]-4F-glutamine (2S, 4R) (1) was taken up in the tumor sites when the myc gene was up-regulated. See FIGS. 3 and 4.

In Vivo Biodistribution Study in Mice

To test the [$^{18}$F]-4F-glutamine isomers as a novel tumor PET imaging agents, we tested the [$^{18}$F]-4F-glutamine (2S, 4R) (1) in normal ICR mice weighing 20-25 grams. 5 mice per group were used for the biodistrubution study. The mice were put under anesthesia with the use of isoflurane and 0.15 mL saline solution containing 25 µCi of each isomer was injected via the lateral tail vein. The mice were sacrificed at 2, 30, 60, 120 and 240 minutes post-injection by cardiac excision while under isoflurane anesthesia. The organs of interest were removed, weighed and the radioactivity was counted with a gamma counter (Packard Cobra). The percent dose per gram was calculated by a comparison of the tissue activity counts to counts of 1.0% of the initial dose. The initial dose consists of 100 times diluted aliquots of the injected material measured at the same rate.

| Biodistribution in normal mice (2, 30, 60 and 120 and 240 min); (2S,4R)-4-F-Gln, 1. % Dose/Gram (n = 5) | | | | | |
|---|---|---|---|---|---|

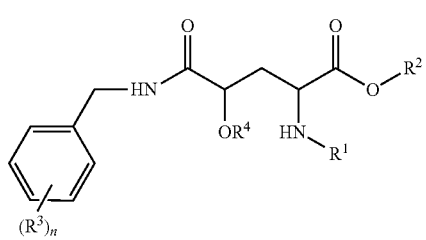

(2S,4R)-4-FGln (1)

| Organ | 2 min | 30 min | 60 min | 120 min | 240 min |
|---|---|---|---|---|---|
| Blood | 6.19 ± 0.83 | 2.72 ± 0.17 | 2.05 ± 0.16 | 0.83 ± 0.12 | 0.48 ± 0.06 |
| Heart | 4.31 ± 0.32 | 3.16 ± 0.25 | 2.86 ± 0.47 | 1.86 ± 0.24 | 1.24 ± 0.19 |
| Muscle | 1.62 ± 0.10 | 2.48 ± 0.16 | 2.86 ± 0.34 | 1.81 ± 0.26 | 0.94 ± 0.15 |
| Lung | 7.15 ± 0.76 | 5.36 ± 0.49 | 4.37 ± 0.28 | 1.69 ± 0.10 | 1.03 ± 0.15 |
| Kidney | 16.1 ± 1.03 | 9.93 ± 0.52 | 7.60 ± 0.84 | 2.15 ± 0.34 | 1.25 ± 0.21 |
| Pancreas | 17.2 ± 1.00 | 19.7 ± 2.16 | 17.5 ± 2.28 | 9.57 ± 1.22 | 5.92 ± 0.87 |
| Spleen | 7.51 ± 0.44 | 5.39 ± 0.72 | 4.22 ± 0.38 | 2.02 ± 0.16 | 1.15 ± 0.14 |
| Liver | 6.92 ± 0.92 | 6.23 ± 0.50 | 5.70 ± 0.62 | 2.46 ± 0.26 | 1.30 ± 0.18 |
| Skin | 2.72 ± 0.05 | 4.01 ± 0.24 | 2.94 ± 0.68 | 2.17 ± 0.16 | 1.25 ± 0.13 |
| Brain | 0.54 ± 0.05 | 0.51 ± 0.05 | 0.53 ± 0.07 | 0.57 ± 0.05 | 0.45 ± 0.06 |
| Bone | 3.93 ± 0.37 | 5.64 ± 0.69 | 7.93 ± 1.02 | 14.4 ± 1.31 | 19.4 ± 0.50 |

A rapid uptake was observed in all major organs, which suggested that the tracer penetrated cell membrane readily following the iv injection. There was a significant heart uptake and a relatively slow washout from the heart tissue. A high initial kidney uptake and fast washout was evident, and it is likely that the urinary excretion was rapid. pancreas displayed the most prominent uptake and retention. the pancreas to liver ratio reached 4 to 1 after 30 min suggesting selective uptake and retention in the pancreas. It may be possible that the exocrine cell in the pancreas cells may have a higher turn-over rate for glutamine. brain uptake is moderate, but the brain uptake value remained constant up to four hrs after injection. There was a significant increase of bond uptake in later time point. It is likely that there was in vivo de-fluorination, which led to the formation of free fluoride ion in the circulating blood. Thus, the increasing bone uptake may be a reflection of in vivo de-fluorination of this tracer.

What is claimed:

1. A single diastereomer of a compound of formula I:

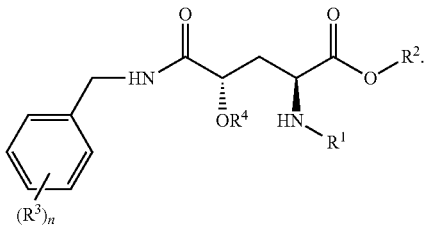

having a diastereomeric excess of at least 80%
wherein
$R^1$ is an acid-labile nitrogen protecting group;
$R^2$ is $C_{1-6}$alkyl or $C_{1-6}$cycloalkyl;
each $R^3$ is independently —$OC_{1-6}$alkyl or $C_{1-6}$cycloalkyl;
$OR^4$ is a leaving group; and
n is 0, 1, 2, 3, or 4.

2. The single diastereomer of claim 1 having a diastereomeric excess of at least 90%.

3. The single diastereomer of claim 1 having a diastereomeric excess of at least 98%.

4. The single diastereomer of claim 1 that is essentially

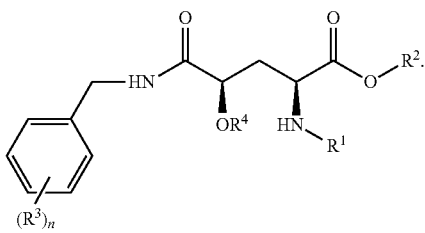

5. The single diastereomer of claim 1 that is essentially

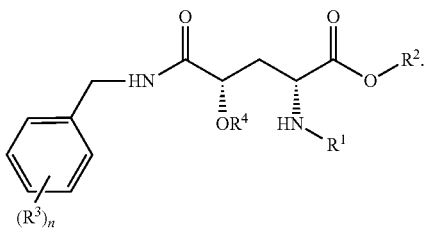

6. The single diastereomer of claim 1 that is essentially

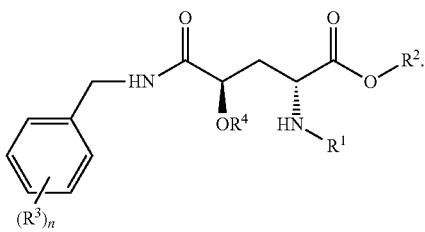

7. The single diastereomer of claim 1 that is essentially

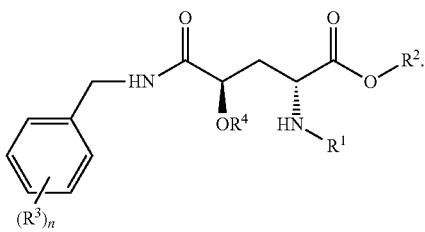

8. The single diastereomer of claim 1, wherein $R^1$ is Boc.
9. The single diastereomer of claim 1, wherein $R^2$ is t-butyl.
10. The single diastereomer of claim 1, wherein each $R^3$ is —$OCH_3$.
11. The single diastereomer of claim 1, wherein n is 3.
12. The single diastereomer of claim 1, wherein $OR^4$ is —OTosylate.

13. The single diastereomer of claim 1 that is essentially

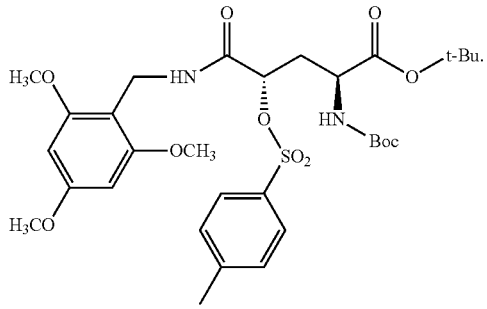 [SMILES: COc1cc(OC)c(CNC(=O)[C@H](C[C@H](NC(=O)OC(C)(C)C)C(=O)OC(C)(C)C)OS(=O)(=O)c2ccc(C)cc2)c(OC)c1]

14. The single diastereomer of claim 1 that is essentially

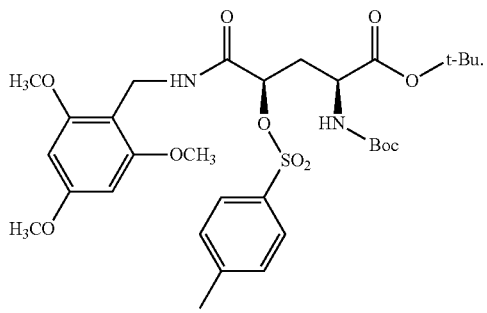 [SMILES: COc1cc(OC)c(CNC(=O)[C@@H](C[C@H](NC(=O)OC(C)(C)C)C(=O)OC(C)(C)C)OS(=O)(=O)c2ccc(C)cc2)c(OC)c1]

15. The single diastereomer of claim 1 that is essentially

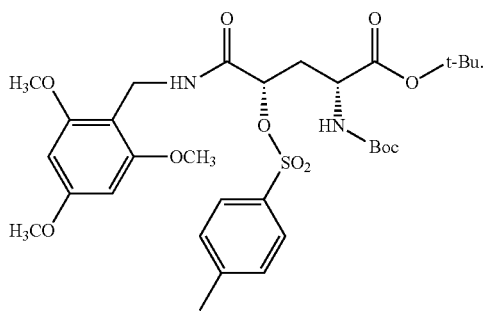 [SMILES: COc1cc(OC)c(CNC(=O)[C@H](C[C@@H](NC(=O)OC(C)(C)C)C(=O)OC(C)(C)C)OS(=O)(=O)c2ccc(C)cc2)c(OC)c1]

16. The single diastereomer of claim 1 that is essentially

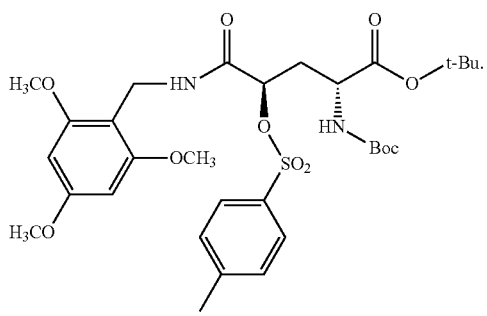 [SMILES: COc1cc(OC)c(CNC(=O)[C@@H](C[C@@H](NC(=O)OC(C)(C)C)C(=O)OC(C)(C)C)OS(=O)(=O)c2ccc(C)cc2)c(OC)c1]

17. A single diastereomer of a compound of formula II

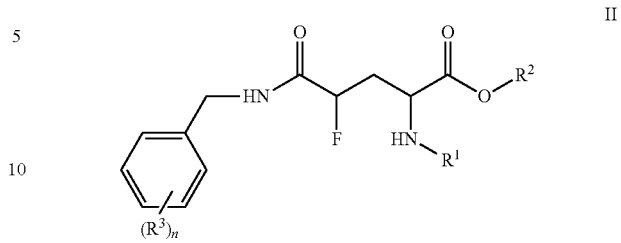

having a diastereomeric excess of at least 80%,
wherein
$R^1$ is an acid-labile nitrogen protecting group;
$R^2$ is $C_{1-6}$alkyl or $C_{1-6}$cycloalkyl;
each $R^3$ is independently —$OC_{1-6}$alkyl or $C_{1-6}$cycloalkyl; and
n is 0, 1, 2, 3, or 4.

18. The single diastereomer of claim 17, wherein $R^1$ is Boc.

19. The single diastereomer of claim 17, wherein $R^2$ is t-butyl.

20. The single diastereomer of claim 17, wherein each $R^3$ is —$OCH_3$.

21. The single diastereomer of claim 17, wherein n is 3.

22. The single diastereomer of claim 17, wherein the F is $^{18}F$.

23. The single diastereomer of claim 17, wherein the compound of formula II is essentially

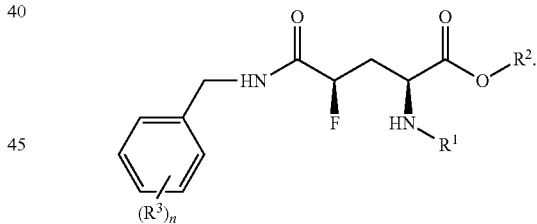

24. The single diastereomer of claim 17, wherein the compound of formula II is essentially

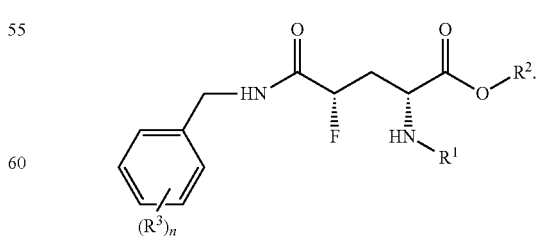

25. The single diastereomer of claim 17, wherein the compound of formula II is essentially

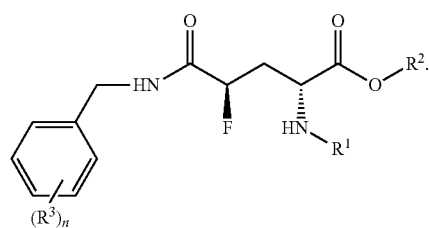
* * * * *